US009277962B2

(12) United States Patent
Koss et al.

(10) Patent No.: US 9,277,962 B2
(45) Date of Patent: *Mar. 8, 2016

(54) IMPEDANCE MEDIATED CONTROL OF POWER DELIVERY FOR ELECTROSURGERY

(75) Inventors: Tim Koss, Palo Alto, CA (US); Miriam H. Taimisto, San Jose, CA (US); Roseanne Varner, Palo Alto, CA (US)

(73) Assignee: Aesculap AG (DE)

( * ) Notice: Subject to any disclaimer, the term of this patent is extended or adjusted under 35 U.S.C. 154(b) by 534 days.

This patent is subject to a terminal disclaimer.

(21) Appl. No.: 13/637,533

(22) PCT Filed: Mar. 25, 2011

(86) PCT No.: PCT/US2011/029958
§ 371 (c)(1),
(2), (4) Date: Jan. 23, 2013

(87) PCT Pub. No.: WO2011/119933
PCT Pub. Date: Sep. 29, 2011

(65) Prior Publication Data
US 2013/0116678 A1 May 9, 2013

Related U.S. Application Data

(63) Continuation of application No. 12/907,646, filed on Oct. 19, 2010, now Pat. No. 8,827,992, which is a continuation-in-part of application No. 12/748,229, filed on Mar. 26, 2010, now Pat. No. 8,419,727.

(51) Int. Cl.
*A61B 18/18* (2006.01)
*A61B 18/12* (2006.01)
(Continued)

(52) U.S. Cl.
CPC ............. *A61B 18/18* (2013.01); *A61B 18/1206* (2013.01); *A61B 18/1445* (2013.01);
(Continued)

(58) Field of Classification Search
CPC ............... A61B 18/1206; A61B 18/18; A61B 18/1445; A61B 2018/00589; A61B 2018/00595; A61B 2018/00642; A61B 2018/00678; A61B 2018/00702; A61B 2018/00875; A61B 2018/0063
See application file for complete search history.

(56) References Cited

U.S. PATENT DOCUMENTS 3,356,408 A   12/1967   Stutz
3,527,224 A    9/1970   Rabinowitz
(Continued)

FOREIGN PATENT DOCUMENTS

CA   2061215 A1   8/1992
CN   1250360      4/2000
(Continued)

OTHER PUBLICATIONS

Japanese Examination Report with English translation issued in related Japanese Application No. JP 2013-501509, dated Nov. 7, 2014.
(Continued)

*Primary Examiner* — Ronald Hupczey, Jr.
*Assistant Examiner* — Amanda Zink
(74) *Attorney, Agent, or Firm* — RatnerPrestia

(57) ABSTRACT

A method of controlling electrosurgical power delivery is based on a comparison of sensed tissue impedance to various impedance threshold values. Energy is delivered to tissue in a sealing cycle as a series of pulses. A pulse has a profile with a preset energy starting value that increases at a ramping rate to a preset end value. Sensed impedance data are monitored throughout each pulse and compared to each of an impedance threshold value for RF setpoint, an impedance threshold value for cumulative time, and an impedance threshold value for energy cutback. Based on sensed impedance during a pulse, the profile of a subsequent pulse can be modified. In the event of a high impedance event that reflects low tissue presence, energy may be cutback. A sealing cycle is stopped when a cumulative amount of time with an impedance value over the impedance cumulative time threshold value reaches a limit.

20 Claims, 9 Drawing Sheets

(51) Int. Cl.
*A61B 18/14* (2006.01)
*A61B 18/00* (2006.01)

(52) U.S. Cl.
CPC .................. *A61B2018/0063* (2013.01); *A61B 2018/00589* (2013.01); *A61B 2018/00595* (2013.01); *A61B 2018/00642* (2013.01); *A61B 2018/00678* (2013.01); *A61B 2018/00702* (2013.01); *A61B 2018/00875* (2013.01)

(56) References Cited

U.S. PATENT DOCUMENTS

| | | | |
|---|---|---|---|
| 3,709,215 A | 1/1973 | Richmond | |
| 3,742,955 A | 7/1973 | Battista | |
| 3,845,771 A | 11/1974 | Vise | |
| 3,920,021 A | 11/1975 | Hiltebrandt | |
| 3,970,088 A | 7/1976 | Morrison | |
| 4,018,230 A | 4/1977 | Ochiai | |
| 4,041,952 A | 8/1977 | Morrison | |
| 4,072,153 A | 2/1978 | Swartz | |
| 4,094,320 A | 6/1978 | Newton | |
| 4,200,104 A | 4/1980 | Harris | |
| 4,231,372 A | 11/1980 | Newton | |
| 4,492,231 A | 1/1985 | Auth | |
| 4,532,924 A | 8/1985 | Auth | |
| 4,590,934 A | 5/1986 | Malis | |
| 4,671,274 A | 6/1987 | Sorochenko | |
| 4,867,649 A | 9/1989 | Kawashima | |
| 4,972,846 A | 11/1990 | Owens | |
| 4,976,717 A | 12/1990 | Boyle | |
| 4,979,948 A | 12/1990 | Geddes | |
| 4,998,527 A | 3/1991 | Meyer | |
| 5,037,379 A | 8/1991 | Clayman | |
| 5,041,101 A | 8/1991 | Seder | |
| 5,059,782 A | 10/1991 | Fukuyama | |
| 5,078,736 A | 1/1992 | Behl | |
| 5,108,408 A | 4/1992 | Lally | |
| 5,133,713 A | 7/1992 | Huang | |
| 5,151,102 A | 9/1992 | Kamiyama | |
| 5,156,613 A | 10/1992 | Sawyer | |
| 5,178,618 A | 1/1993 | Kandarpa | |
| 5,190,541 A | 3/1993 | Abele | |
| 5,207,691 A | 5/1993 | Nardella | |
| 5,217,030 A | 6/1993 | Yoon | |
| 5,234,425 A | 8/1993 | Fogarty | |
| 5,250,074 A | 10/1993 | Wilk | |
| 5,267,998 A | 12/1993 | Hagen | |
| 5,269,780 A | 12/1993 | Roos | |
| 5,269,782 A | 12/1993 | Sutter | |
| 5,273,524 A | 12/1993 | Fox | |
| 5,277,201 A | 1/1994 | Stern | |
| 5,281,216 A | 1/1994 | Kilcek | |
| 5,282,799 A | 2/1994 | Rydell | |
| 5,290,287 A | 3/1994 | Boebel | |
| 5,295,990 A | 3/1994 | Levin | |
| 5,300,068 A | 4/1994 | Rosar | |
| 5,300,087 A | 4/1994 | Knoepfler | |
| 5,312,023 A | 5/1994 | Green | |
| 5,324,289 A | 6/1994 | Eggers | |
| 5,330,471 A | 7/1994 | Eggers | |
| 5,330,502 A | 7/1994 | Hassler | |
| 5,336,229 A | 8/1994 | Noda | |
| 5,336,237 A | 8/1994 | Chin | |
| 5,341,807 A | 8/1994 | Nardella | |
| 5,342,381 A | 8/1994 | Tidemand | |
| 5,352,223 A | 10/1994 | McBrayer | |
| 5,352,235 A | 10/1994 | Koros | |
| 5,354,336 A | 10/1994 | Kelman | |
| 5,356,408 A | 10/1994 | Rydell | |
| 5,374,277 A | 12/1994 | Hassler | |
| 5,377,415 A | 1/1995 | Gibson | |
| 5,391,166 A | 2/1995 | Eggers | |
| 5,395,369 A | 3/1995 | McBrayer | |
| 5,396,900 A | 3/1995 | Slater | |
| 5,397,320 A | 3/1995 | Essig | |
| 5,403,312 A | 4/1995 | Yates | |
| 5,417,687 A | 5/1995 | Nardella | |
| 5,423,809 A * | 6/1995 | Klicek | 606/38 |
| 5,423,814 A | 6/1995 | Zhu | |
| 5,431,676 A | 7/1995 | Dubrul | |
| 5,438,302 A | 8/1995 | Goble | |
| 5,443,463 A | 8/1995 | Stern | |
| 5,443,470 A | 8/1995 | Stern | |
| 5,445,638 A | 8/1995 | Rydell | |
| 5,447,513 A | 9/1995 | Davison | |
| 5,449,355 A | 9/1995 | Rhum | |
| 5,456,684 A | 10/1995 | Schmidt | |
| 5,458,598 A | 10/1995 | Feinberg | |
| 5,462,546 A | 10/1995 | Rydell | |
| 5,472,442 A | 12/1995 | Klicek | |
| 5,480,399 A | 1/1996 | Hebborn | |
| 5,482,054 A | 1/1996 | Slater | |
| 5,484,435 A | 1/1996 | Fleenor | |
| 5,484,436 A | 1/1996 | Eggers | |
| 5,496,312 A | 3/1996 | Klicek | |
| 5,496,317 A | 3/1996 | Goble | |
| 5,514,134 A | 5/1996 | Rydell | |
| 5,520,698 A | 5/1996 | Koh | |
| 5,531,744 A | 7/1996 | Nardella | |
| 5,540,684 A | 7/1996 | Hassler | |
| 5,540,685 A | 7/1996 | Parins | |
| 5,542,945 A | 8/1996 | Fritzsch | |
| 5,549,606 A | 8/1996 | McBrayer | |
| 5,549,637 A | 8/1996 | Cralnich | |
| 5,556,397 A | 9/1996 | Long | |
| 5,558,100 A | 9/1996 | Cox | |
| 5,558,671 A | 9/1996 | Yates | |
| 5,562,700 A | 10/1996 | Huitema | |
| 5,562,701 A | 10/1996 | Huitema | |
| 5,562,702 A | 10/1996 | Huitema | |
| 5,562,720 A | 10/1996 | Stern | |
| 5,564,615 A | 10/1996 | Bishop | |
| 5,569,243 A | 10/1996 | Kortenbach | |
| 5,571,100 A | 11/1996 | Goble | |
| 5,573,535 A | 11/1996 | Viklund | |
| 5,578,052 A | 11/1996 | Koros | |
| 5,599,350 A | 2/1997 | Schulze | |
| 5,601,224 A | 2/1997 | Bishop | |
| 5,603,700 A | 2/1997 | Daneshvar | |
| 5,603,711 A | 2/1997 | Parins | |
| 5,611,803 A | 3/1997 | Heaven | |
| 5,624,452 A | 4/1997 | Yates | |
| 5,637,110 A | 6/1997 | Pennybacker | |
| 5,637,111 A | 6/1997 | Sutcu | |
| 5,653,692 A | 8/1997 | Masterson | |
| 5,658,281 A | 8/1997 | Heard | |
| 5,662,662 A | 9/1997 | Bishop | |
| 5,662,676 A | 9/1997 | Koninckx | |
| 5,665,085 A | 9/1997 | Nardella | |
| 5,665,100 A | 9/1997 | Yoon | |
| 5,667,526 A | 9/1997 | Levin | |
| 5,669,907 A | 9/1997 | Platt | |
| 5,673,840 A | 10/1997 | Schulze | |
| 5,673,841 A | 10/1997 | Schulze | |
| 5,674,184 A | 10/1997 | Hassler | |
| 5,674,220 A | 10/1997 | Fox | |
| 5,675,184 A | 10/1997 | Matsubayashi | |
| 5,680,982 A | 10/1997 | Schulze | |
| 5,681,282 A | 10/1997 | Eggers | |
| 5,683,385 A | 11/1997 | Kortenbach | |
| 5,683,388 A | 11/1997 | Slater | |
| 5,688,270 A | 11/1997 | Yates | |
| 5,693,051 A | 12/1997 | Schulze | |
| 5,697,949 A | 12/1997 | Giurtino | |
| 5,700,261 A | 12/1997 | Brinkerhoff | |
| 5,702,390 A | 12/1997 | Austin | |
| 5,704,534 A | 1/1998 | Hultema | |
| 5,707,369 A | 1/1998 | Vaitekunas | |
| 5,709,680 A | 1/1998 | Yates | |
| 5,713,896 A | 2/1998 | Nardella | |
| 5,715,832 A | 2/1998 | Koblish | |
| 5,718,703 A | 2/1998 | Chin | |
| 5,720,719 A | 2/1998 | Edwards | |
| 5,728,143 A | 3/1998 | Gough | |

(56) References Cited

U.S. PATENT DOCUMENTS

| | | |
|---|---|---|
| 5,733,283 A | 3/1998 | Malis |
| 5,735,289 A | 4/1998 | Pfeffer |
| 5,735,848 A | 4/1998 | Yates |
| 5,735,849 A | 4/1998 | Baden |
| 5,741,285 A | 4/1998 | McBrayer |
| 5,743,906 A | 4/1998 | Parins |
| 5,746,750 A | 5/1998 | Prestel |
| 5,749,895 A | 5/1998 | Sawyer |
| 5,755,717 A | 5/1998 | Yates |
| 5,769,849 A | 6/1998 | Eggers |
| 5,776,130 A | 7/1998 | Buysse |
| 5,788,662 A | 8/1998 | Antanavich |
| 5,797,906 A | 8/1998 | Rhum |
| 5,797,941 A | 8/1998 | Schulze |
| 5,810,811 A | 9/1998 | Yates |
| 5,817,091 A | 10/1998 | Nardella |
| 5,817,092 A | 10/1998 | Behl |
| 5,823,066 A | 10/1998 | Huitema |
| 5,833,689 A | 11/1998 | Long |
| 5,833,690 A | 11/1998 | Yates |
| 5,836,990 A | 11/1998 | Li |
| 5,840,077 A | 11/1998 | Rowden |
| 5,855,576 A | 1/1999 | LeVeen |
| 5,860,975 A | 1/1999 | Goble |
| 5,891,142 A | 4/1999 | Eggers |
| 5,893,835 A | 4/1999 | Witt |
| 5,893,874 A | 4/1999 | Bourque |
| 5,931,835 A | 8/1999 | Mackey |
| 5,931,836 A | 8/1999 | Hatta |
| 5,954,720 A | 9/1999 | Wilson |
| 5,976,128 A | 11/1999 | Schilling |
| 5,979,453 A | 11/1999 | Savage |
| 6,003,517 A | 12/1999 | Sheffield |
| 6,004,319 A | 12/1999 | Goble |
| 6,030,384 A | 2/2000 | Nezhat |
| 6,039,735 A | 3/2000 | Greep |
| 6,050,993 A | 4/2000 | Tu |
| 6,050,995 A | 4/2000 | Durgin |
| 6,056,744 A | 5/2000 | Edwards |
| 6,056,746 A | 5/2000 | Goble |
| 6,059,766 A | 5/2000 | Greff |
| 6,059,782 A | 5/2000 | Novak |
| 6,066,139 A | 5/2000 | Ryan |
| 6,068,626 A | 5/2000 | Harrington |
| 6,071,281 A | 6/2000 | Burnside |
| 6,074,386 A | 6/2000 | Goble |
| 6,086,586 A | 7/2000 | Hooven |
| 6,090,106 A | 7/2000 | Goble |
| 6,093,186 A | 7/2000 | Goble |
| 6,096,037 A | 8/2000 | Muller |
| 6,099,550 A | 8/2000 | Yoon |
| 6,123,701 A | 9/2000 | Nezhat |
| H1904 H | 10/2000 | Yates |
| 6,142,992 A * | 11/2000 | Cheng et al. ............... 606/34 |
| 6,152,920 A | 11/2000 | Thompson |
| 6,152,932 A | 11/2000 | Ternstrom |
| 6,162,220 A | 12/2000 | Nezhat |
| 6,174,309 B1 | 1/2001 | Wrublewski |
| 6,179,832 B1 | 1/2001 | Jones |
| 6,203,541 B1 | 3/2001 | Keppel |
| 6,203,542 B1 | 3/2001 | Ellsberry |
| 6,206,877 B1 | 3/2001 | Kese |
| 6,210,406 B1 | 4/2001 | Webster |
| 6,212,426 B1 | 4/2001 | Swanson |
| 6,217,894 B1 | 4/2001 | Sawhney |
| 6,228,084 B1 | 5/2001 | Kirwan |
| 6,234,178 B1 | 5/2001 | Goble |
| 6,241,139 B1 | 6/2001 | Milliman |
| 6,245,069 B1 | 6/2001 | Gminder |
| 6,254,601 B1 | 7/2001 | Burbank |
| 6,258,085 B1 | 7/2001 | Eggleston |
| 6,277,114 B1 | 8/2001 | Bultivant |
| 6,283,963 B1 | 9/2001 | Regula |
| 6,287,304 B1 | 9/2001 | Eggers |
| 6,290,715 B1 | 9/2001 | Sharkey |
| 6,293,942 B1 | 9/2001 | Goble |
| 6,293,946 B1 | 9/2001 | Thorne |
| 6,296,636 B1 | 10/2001 | Cheng |
| 6,306,134 B1 | 10/2001 | Goble |
| 6,312,430 B1 | 11/2001 | Wilson |
| 6,322,494 B1 | 11/2001 | Bullivant |
| 6,327,505 B1 | 12/2001 | Medhkour |
| 6,334,861 B1 | 1/2002 | Chandler |
| 6,350,274 B1 | 2/2002 | Li |
| 6,361,559 B1 | 3/2002 | Houser |
| 6,364,879 B1 | 4/2002 | Chen |
| 6,371,956 B1 | 4/2002 | Wilson |
| 6,391,024 B1 | 5/2002 | Sun |
| 6,391,029 B1 | 5/2002 | Hooven |
| 6,398,779 B1 | 6/2002 | Buysse et al. |
| 6,398,781 B1 | 6/2002 | Goble |
| H2037 H | 7/2002 | Yates |
| 6,416,509 B1 | 7/2002 | Goble |
| 6,423,057 B1 | 7/2002 | He |
| 6,428,550 B1 | 8/2002 | Vargas |
| 6,436,096 B1 | 8/2002 | Hareyama |
| 6,440,130 B1 | 8/2002 | Mulier |
| 6,443,952 B1 | 9/2002 | Mulier |
| 6,464,702 B2 | 10/2002 | Schulze |
| 6,485,486 B1 | 11/2002 | Trembly |
| 6,485,489 B2 | 11/2002 | Teirstein |
| 6,491,690 B1 | 12/2002 | Goble |
| 6,494,881 B1 | 12/2002 | Bales |
| 6,500,176 B1 | 12/2002 | Truckai |
| 6,514,252 B2 | 2/2003 | Nezhat |
| 6,517,530 B1 | 2/2003 | Kleven |
| 6,520,185 B1 | 2/2003 | Bommannan |
| 6,533,784 B2 | 3/2003 | Truckai |
| 6,546,933 B1 | 4/2003 | Yoon |
| 6,554,829 B2 | 4/2003 | Schulze |
| 6,564,806 B1 | 5/2003 | Fogarty |
| 6,565,560 B1 | 5/2003 | Goble |
| 6,565,561 B1 | 5/2003 | Goble |
| 6,584,360 B2 | 6/2003 | Francischelli |
| 6,610,060 B2 | 8/2003 | Mulier |
| 6,610,074 B2 | 8/2003 | Santili |
| 6,613,048 B2 | 9/2003 | Mulier |
| 6,616,654 B2 | 9/2003 | Mollenauer |
| 6,616,659 B1 | 9/2003 | de la Torre |
| 6,619,529 B2 | 9/2003 | Green |
| 6,623,482 B2 | 9/2003 | Pendekantl |
| 6,626,901 B1 | 9/2003 | Treat |
| 6,645,198 B1 | 11/2003 | Bommannan |
| 6,645,201 B1 | 11/2003 | Utley |
| 6,648,839 B2 | 11/2003 | Manna |
| 6,652,518 B2 | 11/2003 | Wellman |
| 6,656,177 B2 | 12/2003 | Truckai |
| 6,666,859 B1 | 12/2003 | Fleenor |
| 6,673,085 B1 | 1/2004 | Berg |
| 6,676,660 B2 | 1/2004 | Wampler |
| 6,682,526 B1 | 1/2004 | Jones |
| 6,682,527 B2 | 1/2004 | Strut |
| 6,695,840 B2 | 2/2004 | Schulze |
| 6,699,245 B2 | 3/2004 | Dinger |
| 6,719,754 B2 | 4/2004 | Underwood |
| 6,722,371 B1 | 4/2004 | Fogarty |
| 6,726,682 B2 | 4/2004 | Harrington |
| 6,736,814 B2 | 5/2004 | Manna |
| 6,743,229 B2 | 6/2004 | Buysse |
| 6,746,488 B1 | 6/2004 | Bales |
| 6,752,154 B2 | 6/2004 | Fogarty |
| 6,752,803 B2 | 6/2004 | Goldman |
| 6,755,827 B2 | 6/2004 | Mulier |
| 6,770,070 B1 | 8/2004 | Balbierz |
| 6,770,072 B1 | 8/2004 | Truckai |
| 6,773,435 B2 | 8/2004 | Schulze |
| 6,776,780 B2 | 8/2004 | Mulier |
| 6,796,981 B2 * | 9/2004 | Wham et al. ............... 606/34 |
| 6,808,525 B2 | 10/2004 | Latterell |
| 6,817,974 B2 | 11/2004 | Cooper |
| 6,821,273 B2 | 11/2004 | Mollenauer |
| 6,837,888 B2 | 1/2005 | Ciarrocca |
| 6,840,938 B1 | 1/2005 | Morley |
| 6,843,789 B2 | 1/2005 | Goble |

(56) References Cited

U.S. PATENT DOCUMENTS

| | | |
|---|---|---|
| 6,852,108 B2 | 2/2005 | Barry |
| 6,858,028 B2 | 2/2005 | Mulier |
| 6,889,089 B2 | 5/2005 | Behl |
| 6,893,435 B2 | 5/2005 | Goble |
| 6,896,672 B1 | 5/2005 | Eggers |
| 6,896,673 B2 | 5/2005 | Hooven |
| 6,902,536 B2 | 6/2005 | Manna |
| 6,905,506 B2 | 6/2005 | Burbank |
| 6,908,463 B2 | 6/2005 | Treat |
| 6,913,579 B2 | 7/2005 | Truckai |
| 6,918,907 B2 | 7/2005 | Kelly |
| 6,918,909 B2 | 7/2005 | Ohyama |
| 6,923,803 B2 | 8/2005 | Goble |
| 6,923,806 B2 | 8/2005 | Hooven |
| 6,926,712 B2 | 8/2005 | Phan |
| 6,929,642 B2 | 8/2005 | Xiao |
| 6,936,048 B2 | 8/2005 | Hurst |
| 6,939,346 B2 | 9/2005 | Kannenberg |
| 6,953,461 B2 | 10/2005 | McClurken |
| 6,981,628 B2 | 1/2006 | Wales |
| 7,008,421 B2 | 3/2006 | Daniel |
| 7,033,356 B2 | 4/2006 | Latterell |
| 7,063,699 B2 | 6/2006 | Hess |
| 7,090,637 B2 | 8/2006 | Danitz |
| 7,090,673 B2 | 8/2006 | Dycus |
| 7,090,685 B2 | 8/2006 | Kortenbach |
| 7,094,235 B2 | 8/2006 | Francischelli |
| 7,101,371 B2 | 9/2006 | Dycus |
| 7,101,372 B2 | 9/2006 | Dycus |
| 7,101,373 B2 | 9/2006 | Dycus |
| 7,118,587 B2 | 10/2006 | Dycus |
| 7,125,409 B2 | 10/2006 | Truckai |
| 7,137,980 B2 | 11/2006 | Buysse |
| 7,159,750 B2 | 1/2007 | Racenet |
| 7,166,102 B2 | 1/2007 | Fleenor |
| 7,169,146 B2 | 1/2007 | Truckai |
| 7,179,254 B2 | 2/2007 | Pendekanti |
| 7,195,627 B2 | 3/2007 | Amoah |
| 7,220,260 B2 | 5/2007 | Fleming |
| 7,238,195 B2 | 7/2007 | Viola |
| 7,250,048 B2 | 7/2007 | Francischelli |
| 7,255,697 B2 | 8/2007 | Dycus |
| 7,267,677 B2 | 9/2007 | Johnson |
| 7,270,664 B2 | 9/2007 | Johnson |
| 7,276,068 B2 | 10/2007 | Johnson |
| 7,278,991 B2 | 10/2007 | Morris |
| 7,291,143 B2 | 11/2007 | Swanson |
| 7,303,557 B2 * | 12/2007 | Wham et al. .................... 606/34 |
| 7,329,256 B2 | 2/2008 | Johnson |
| 7,364,577 B2 | 4/2008 | Wham |
| 7,367,972 B2 | 5/2008 | Francischelli |
| 7,410,483 B2 | 8/2008 | Danitz |
| 7,494,039 B2 | 2/2009 | Racenet |
| 7,506,790 B2 | 3/2009 | Shelton |
| 7,513,898 B2 | 4/2009 | Johnson |
| 7,540,872 B2 | 6/2009 | Schechter |
| 7,549,564 B2 | 6/2009 | Boudreaux |
| 7,588,566 B2 | 9/2009 | Treat |
| 7,624,902 B2 | 12/2009 | Marczyk |
| 7,641,651 B2 | 1/2010 | Nezhat |
| 7,651,492 B2 | 1/2010 | Wham |
| 7,703,653 B2 | 4/2010 | Shah |
| 7,794,461 B2 | 9/2010 | Eder |
| 7,803,156 B2 | 9/2010 | Eder |
| 7,862,565 B2 | 1/2011 | Eder |
| 8,147,485 B2 * | 4/2012 | Wham et al. .................... 606/34 |
| 2001/0029367 A1 | 10/2001 | Fleenor |
| 2002/0062123 A1 | 5/2002 | McClurken |
| 2002/0062136 A1 | 5/2002 | Hillstead |
| 2002/0107514 A1 | 8/2002 | Hooven |
| 2002/0124853 A1 | 9/2002 | Burbank |
| 2002/0128643 A1 | 9/2002 | Simpson |
| 2002/0151882 A1 | 10/2002 | Marko |
| 2002/0177848 A1 | 11/2002 | Truckai |
| 2002/0183734 A1 | 12/2002 | Bommannan |
| 2002/0183738 A1 | 12/2002 | Chee |
| 2003/0004510 A1 * | 1/2003 | Wham et al. .................... 606/51 |
| 2003/0015855 A1 | 1/2003 | McCoy et al. |
| 2003/0018331 A1 | 1/2003 | Dycus |
| 2003/0078577 A1 | 4/2003 | Truckai |
| 2003/0144652 A1 | 7/2003 | Baker |
| 2003/0144653 A1 | 7/2003 | Francischelli |
| 2003/0153908 A1 | 8/2003 | Goble |
| 2003/0158547 A1 | 8/2003 | Phan |
| 2003/0158551 A1 * | 8/2003 | Paton et al. .................... 606/51 |
| 2003/0171745 A1 | 9/2003 | Francischelli |
| 2003/0199863 A1 | 10/2003 | Swanson |
| 2003/0199869 A1 | 10/2003 | Johnson |
| 2003/0216726 A1 | 11/2003 | Eggers |
| 2003/0229344 A1 | 12/2003 | Dycus |
| 2003/0236549 A1 | 12/2003 | Bonadio |
| 2004/0006339 A1 | 1/2004 | Underwood |
| 2004/0010245 A1 | 1/2004 | Cerier |
| 2004/0049185 A1 | 3/2004 | Latterell |
| 2004/0068274 A1 | 4/2004 | Hooven |
| 2004/0097919 A1 | 5/2004 | Wellman |
| 2004/0106917 A1 | 6/2004 | Ormsby |
| 2004/0122423 A1 | 6/2004 | Dycus |
| 2004/0143263 A1 | 7/2004 | Schechter |
| 2004/0167508 A1 * | 8/2004 | Wham et al. .................... 606/32 |
| 2004/0193148 A1 * | 9/2004 | Wham et al. .................... 606/40 |
| 2004/0199226 A1 | 10/2004 | Shadduck |
| 2004/0236320 A1 | 11/2004 | Protsenko |
| 2004/0236326 A1 | 11/2004 | Schulze |
| 2005/0010212 A1 | 1/2005 | McClurken |
| 2005/0015085 A1 | 1/2005 | McClurken |
| 2005/0019654 A1 | 1/2005 | Kishida |
| 2005/0021024 A1 | 1/2005 | Hooven |
| 2005/0021026 A1 | 1/2005 | Baily |
| 2005/0021027 A1 | 1/2005 | Shields |
| 2005/0033276 A1 | 2/2005 | Adachi |
| 2005/0033277 A1 | 2/2005 | Clague |
| 2005/0033278 A1 | 2/2005 | McClurken |
| 2005/0033282 A1 | 2/2005 | Hooven |
| 2005/0070895 A1 | 3/2005 | Ryan |
| 2005/0070978 A1 | 3/2005 | Bek |
| 2005/0090819 A1 | 4/2005 | Goble |
| 2005/0096645 A1 | 5/2005 | Wellman |
| 2005/0096694 A1 | 5/2005 | Lee |
| 2005/0101951 A1 * | 5/2005 | Wham et al. .................... 606/51 |
| 2005/0107781 A1 | 5/2005 | Ostrovsky |
| 2005/0107784 A1 | 5/2005 | Moses |
| 2005/0113817 A1 | 5/2005 | Isaacson |
| 2005/0113820 A1 | 5/2005 | Goble |
| 2005/0113826 A1 | 5/2005 | Johnson |
| 2005/0119654 A1 | 6/2005 | Swanson |
| 2005/0131390 A1 | 6/2005 | Heinrich |
| 2005/0137591 A1 | 6/2005 | Barry |
| 2005/0149073 A1 | 7/2005 | Arani |
| 2005/0171530 A1 | 8/2005 | Hooven |
| 2005/0171533 A1 | 8/2005 | Latterell |
| 2005/0187561 A1 | 8/2005 | Lee-Sepsick |
| 2005/0192568 A1 | 9/2005 | Truckai |
| 2005/0192633 A1 | 9/2005 | Montpetit |
| 2005/0196421 A1 | 9/2005 | Hunter |
| 2005/0203500 A1 | 9/2005 | Saadat |
| 2005/0203504 A1 | 9/2005 | Wham |
| 2005/0209664 A1 | 9/2005 | Hunter |
| 2005/0226682 A1 | 10/2005 | Chersky |
| 2005/0256522 A1 | 11/2005 | Francischelli |
| 2005/0256524 A1 | 11/2005 | Long |
| 2005/0259035 A1 | 11/2005 | Iwaki |
| 2005/0261676 A1 | 11/2005 | Hall |
| 2006/0025765 A1 | 2/2006 | Landman |
| 2006/0025812 A1 | 2/2006 | Shelton |
| 2006/0041254 A1 | 2/2006 | Francischelli |
| 2006/0052778 A1 | 3/2006 | Chapman |
| 2006/0052779 A1 | 3/2006 | Hammill |
| 2006/0064084 A1 | 3/2006 | Haemmerich |
| 2006/0064085 A1 | 3/2006 | Schechter |
| 2006/0064086 A1 | 3/2006 | Odom |
| 2006/0079872 A1 | 4/2006 | Eggleston |
| 2006/0142751 A1 | 6/2006 | Treat |
| 2006/0167451 A1 | 7/2006 | Cropper |

(56) References Cited

U.S. PATENT DOCUMENTS

| | | |
|---|---|---|
| 2006/0189980 A1 | 8/2006 | Johnson |
| 2006/0190029 A1 | 8/2006 | Wales |
| 2006/0199999 A1 | 9/2006 | Ikeda |
| 2006/0217709 A1 | 9/2006 | Couture |
| 2006/0226196 A1 | 10/2006 | Hueil |
| 2006/0229665 A1 | 10/2006 | Wales |
| 2006/0253117 A1 | 11/2006 | Hovda |
| 2006/0258954 A1 | 11/2006 | Timberlake |
| 2006/0259034 A1 | 11/2006 | Eder |
| 2006/0259035 A1 | 11/2006 | Nezhat |
| 2006/0271037 A1 | 11/2006 | Maroney |
| 2006/0271038 A1 | 11/2006 | Johnson |
| 2006/0271041 A1 | 11/2006 | Eder |
| 2006/0271042 A1 | 11/2006 | Latterell |
| 2006/0287674 A1 | 12/2006 | Ginn |
| 2006/0289602 A1 | 12/2006 | Wales |
| 2006/0293649 A1 | 12/2006 | Lorang et al. |
| 2006/0293655 A1 | 12/2006 | Sartor |
| 2007/0005053 A1 | 1/2007 | Dando |
| 2007/0005061 A1 | 1/2007 | Eder |
| 2007/0055231 A1 | 3/2007 | Dycus |
| 2007/0062017 A1 | 3/2007 | Dycus |
| 2007/0073340 A1 | 3/2007 | Shelton |
| 2007/0128174 A1 | 6/2007 | Kleinsek |
| 2007/0129726 A1 | 6/2007 | Eder |
| 2007/0173803 A1 | 7/2007 | Wham et al. |
| 2007/0173804 A1 | 7/2007 | Wham |
| 2007/0173805 A1 | 7/2007 | Weinberg et al. |
| 2007/0173811 A1 | 7/2007 | Couture |
| 2007/0179497 A1 | 8/2007 | Eggers |
| 2007/0185482 A1 | 8/2007 | Eder |
| 2007/0208330 A1 | 9/2007 | Treat |
| 2007/0244538 A1 | 10/2007 | Eder |
| 2007/0250113 A1 | 10/2007 | Hegeman |
| 2007/0260242 A1 | 11/2007 | Dycus |
| 2007/0265613 A1 | 11/2007 | Edelstein |
| 2007/0282318 A1 | 12/2007 | Spooner |
| 2007/0282320 A1 | 12/2007 | Buysse |
| 2007/0299439 A1 | 12/2007 | Latterell |
| 2008/0015562 A1 | 1/2008 | Hong et al. |
| 2008/0039835 A1 | 2/2008 | Johnson |
| 2008/0045947 A1 | 2/2008 | Johnson |
| 2008/0114351 A1 | 5/2008 | Irisawa et al. |
| 2008/0114356 A1 | 5/2008 | Johnson |
| 2008/0172052 A1 | 7/2008 | Eder |
| 2008/0188844 A1 | 8/2008 | McGreevy |
| 2008/0195093 A1 | 8/2008 | Couture |
| 2008/0221565 A1 | 9/2008 | Eder |
| 2008/0228179 A1 | 9/2008 | Eder |
| 2008/0275446 A1 | 11/2008 | Messerly |
| 2008/0308607 A1 | 12/2008 | Timm |
| 2009/0018535 A1 | 1/2009 | Schechter |
| 2009/0138006 A1 | 5/2009 | Bales |
| 2009/0149853 A1 | 6/2009 | Shields |
| 2009/0157071 A1 | 6/2009 | Wham |
| 2009/0157072 A1 | 6/2009 | Wham |
| 2009/0157075 A1 | 6/2009 | Wham |
| 2009/0171354 A1 | 7/2009 | Deville |
| 2009/0182323 A1 | 7/2009 | Eder |
| 2009/0198272 A1 | 8/2009 | Kerver |
| 2009/0209953 A1 | 8/2009 | Schoenman |
| 2009/0234347 A1 | 9/2009 | Treat |
| 2009/0240245 A1 | 9/2009 | Deville |
| 2009/0299367 A1 | 12/2009 | Ginnebaugh |
| 2010/0042093 A9 | 2/2010 | Wham |
| 2010/0076427 A1 | 3/2010 | Heard |
| 2010/0094282 A1 | 4/2010 | Kabaya |
| 2010/0280508 A1 | 11/2010 | Eder |
| 2010/0298823 A1 | 11/2010 | Cao |
| 2011/0202058 A1 | 8/2011 | Eder |

FOREIGN PATENT DOCUMENTS

| | | |
|---|---|---|
| CN | 1882289 | 12/2006 |
| EP | 0440385 A2 | 8/1991 |
| EP | 0487269 A1 | 5/1992 |
| EP | 0502268 A1 | 9/1992 |
| EP | 0562195 A1 | 9/1993 |
| EP | 0658333 A1 | 6/1995 |
| EP | 536998 | 4/1996 |
| EP | 518230 | 5/1996 |
| EP | 878169 | 11/1998 |
| EP | 640315 | 12/1998 |
| EP | 0923907 A1 | 6/1999 |
| EP | 640317 | 9/1999 |
| EP | 771176 | 7/2000 |
| EP | 1050278 | 11/2000 |
| EP | 0833593 B1 | 2/2001 |
| EP | 1254637 | 11/2002 |
| EP | 0737446 B1 | 12/2002 |
| EP | 0717960 B1 | 2/2003 |
| EP | 0869742 B1 | 5/2003 |
| EP | 1330989 | 7/2003 |
| EP | 1330991 | 7/2003 |
| EP | 1344498 | 9/2003 |
| EP | 0873089 B1 | 10/2003 |
| EP | 0742696 B1 | 11/2003 |
| EP | 1041933 B1 | 3/2004 |
| EP | 959784 | 4/2004 |
| EP | 0794735 | 7/2004 |
| EP | 1004277 B1 | 7/2004 |
| EP | 0959786 B1 | 9/2004 |
| EP | 0913126 B1 | 10/2004 |
| EP | 0956827 B1 | 10/2004 |
| EP | 1472984 A1 | 11/2004 |
| EP | 1025807 | 12/2004 |
| EP | 927543 | 4/2005 |
| EP | 1586281 | 10/2005 |
| EP | 1621146 A2 | 2/2006 |
| EP | 1637086 | 3/2006 |
| EP | 1645234 | 4/2006 |
| EP | 1645237 A1 | 4/2006 |
| EP | 0875209 B1 | 5/2006 |
| EP | 1293170 B1 | 6/2006 |
| EP | 1293169 B1 | 7/2006 |
| EP | 1064886 B1 | 8/2006 |
| EP | 1767164 A1 | 3/2007 |
| EP | 1518498 B1 | 12/2007 |
| EP | 1862138 A1 | 12/2007 |
| EP | 1039862 B1 | 5/2008 |
| EP | 1532933 B1 | 5/2008 |
| EP | 1707143 B1 | 6/2008 |
| EP | 1518499 B1 | 8/2008 |
| EP | 1958583 | 8/2008 |
| EP | 1632192 B1 | 3/2009 |
| EP | 2065006 | 6/2009 |
| EP | 1486177 B1 | 8/2009 |
| EP | 1852081 B1 | 8/2009 |
| EP | 1747761 B1 | 10/2009 |
| EP | 2110093 | 10/2009 |
| EP | 2106764 A2 | 10/2012 |
| JP | 9-501328 | 10/1994 |
| JP | 11070123 | 3/1999 |
| JP | 11070124 | 3/1999 |
| JP | 2001518344 | 10/2001 |
| JP | 2003088534 A | 3/2003 |
| JP | 2004049566 A | 2/2004 |
| JP | 2005021703 | 1/2005 |
| JP | 2005 040616 A | 2/2005 |
| JP | 2005512671 | 5/2005 |
| JP | 2005144193 A | 6/2005 |
| JP | 20050517498 A | 6/2005 |
| JP | 2007 195973 A | 8/2007 |
| JP | 2008 114042 A | 5/2008 |
| WO | WO-9222257 A1 | 12/1992 |
| WO | WO-9308754 A1 | 5/1993 |
| WO | WO-9400060 A1 | 1/1994 |
| WO | WO 94/26228 | 11/1994 |
| WO | WO-9426179 A1 | 11/1994 |
| WO | WO-9502371 A2 | 1/1995 |

(56) References Cited

FOREIGN PATENT DOCUMENTS

| | | |
|---|---|---|
| WO | 9509576 | 4/1995 |
| WO | 9514436 | 6/1995 |
| WO | 9525471 | 9/1995 |
| WO | WO-9605776 A1 | 2/1996 |
| WO | 9619152 | 6/1996 |
| WO | WO-9616605 A1 | 6/1996 |
| WO | WO-9623449 A1 | 8/1996 |
| WO | 9724995 | 7/1997 |
| WO | WO-9724073 A1 | 7/1997 |
| WO | WO-9724074 A1 | 7/1997 |
| WO | WO-9812999 A2 | 4/1998 |
| WO | WO-9843548 A1 | 10/1998 |
| WO | WO-9853750 A1 | 12/1998 |
| WO | 9917670 | 4/1999 |
| WO | WO-9923933 A2 | 5/1999 |
| WO | 9951155 | 10/1999 |
| WO | 9951158 | 10/1999 |
| WO | WO-9952459 A1 | 10/1999 |
| WO | WO-9956646 A1 | 11/1999 |
| WO | WO-0013192 A1 | 3/2000 |
| WO | WO-0013193 A1 | 3/2000 |
| WO | 0047124 | 8/2000 |
| WO | 0051512 | 9/2000 |
| WO | WO-0112090 A1 | 2/2001 |
| WO | WO-0135846 A1 | 5/2001 |
| WO | WO-0154602 A2 | 8/2001 |
| WO | WO-0158373 A1 | 8/2001 |
| WO | WO-0182812 A1 | 11/2001 |
| WO | WO-0224092 A1 | 3/2002 |
| WO | 0236028 | 5/2002 |
| WO | WO-02058542 A2 | 8/2002 |
| WO | 02071926 | 9/2002 |
| WO | WO-02067798 A1 | 9/2002 |
| WO | 03024348 | 3/2003 |
| WO | 03053266 | 7/2003 |
| WO | WO-03088806 A2 | 10/2003 |
| WO | 03096886 | 11/2003 |
| WO | WO-03103522 A1 | 12/2003 |
| WO | WO-2004032596 A2 | 4/2004 |
| WO | WO-2004032776 A1 | 4/2004 |
| WO | WO-0158372 A1 | 8/2004 |
| WO | WO-2004073490 A2 | 9/2004 |
| WO | WO-2004098383 A2 | 11/2004 |
| WO | 2004103156 | 12/2004 |
| WO | WO-2005009213 A2 | 2/2005 |
| WO | 2005030071 | 4/2005 |
| WO | 2005034729 | 4/2005 |
| WO | WO-2005034729 A2 | 4/2005 |
| WO | WO-2005079901 A1 | 9/2005 |
| WO | WO-2005115251 A1 | 12/2005 |
| WO | WO-2006060431 A1 | 6/2006 |
| WO | 2006124518 | 11/2006 |
| WO | 2006124601 | 11/2006 |
| WO | WO-2007002227 A2 | 1/2007 |
| WO | WO-2007082061 A2 | 7/2007 |
| WO | 2008094564 | 8/2008 |
| WO | WO-2008094554 A2 | 8/2008 |
| WO | WO-2008124112 A1 | 10/2008 |
| WO | 2009070780 | 6/2009 |
| WO | 2009154976 | 12/2009 |

OTHER PUBLICATIONS

Chinese Notice of First Office Action with Text of Office Action issued in related Chinese Application No. 201180009484.0, dated Sep. 29, 2014.
Japanese Examination Report issued in related Japanese Application No. 2011-509759 dated Feb. 28, 2014.
Indian Examination Report issued in related Indian Application No. 4341/KOLNP/2007 dated Feb. 27, 2014.
Korean Examination report issued in related Korean Application No. 10-2009-7018104 dated Feb. 20, 2014.
Notice of Allowance for U.S. Appl. No. 13/096,912, dated Jul. 25, 2014.
Office Action for U.S. Appl. No. 12/121,734, dated Sep. 17, 2014.
U.S. Appl. No. 13/070,391, filed Mar. 23, 2011.
U.S. Appl. No. 08/948,282, filed Oct. 9, 1997.
U.S. Appl. No. 12/200,798, filed Aug. 28, 2008.
U.S. Appl. No. 13/110,848, filed May 18, 2011.
U.S. Appl. No. 13/021,633, filed Feb. 4, 2011.
U.S. Appl. No. 12/748,229, filed Feb. 4, 2011.
International Application Serial No. PCT/US2011/029958, International Search Report dated Dec. 22, 2011.
"Seal Open Forceps (Product Information)", GYRUS Medical, downloaded Oct. 5, 2005.
"Enable Medical Introduces Second Generation Bipolar Scissors", Health Industry Today, (Dec. 1998).
"U.S. Patent Issued for Novare Surgical Systems Cygnet Surgical Clamp: Novare Signs Multi-Year Supply Agreement with Boston Scientific", PR Newswire, (Sep. 2, 2003).
"ERBE BiClamp Brochure", http://www.erbe-med.com/erbe/media/Marketingmateriallen/85100-139_ERBE_EN_BiClamp_D024676.pdf, 6 pgs.
"Curon Announces the Publication of Data Supporting Durability and Effectiveness of STRETTA System—Positive One Year Follow-Up Data of U.S. Clinical Trial Published in Gastrointestinal Endoscopy", PR Newswire, NYTH10307022002, (Feb. 7, 2002).
"Arthrocare Receives Clearance to Market Coblation-Based Devices for Gynecology and Laparoscopic Surgery: Clearance Includes Plasma Forceps and 21 Specific Indications", Business Wire, (Oct. 25, 2001), 524.
"SURGRX 510(K) Summary (# K031133)", Palo Alto, CA, (Jul. 3, 2003), 5 pgs.
"LP Scissors (Product Information)", GYRUS Medical, downloaded Oct. 5, 2005.
"Radiofrequency Energy Proven Effective Against Leading Cause of Obstructive Sleep Apnea", Business Wire, 09140175, (Sep. 14, 1998).
"A New Thermal Device for Sealing and Dividing Blood Vessel", Treat, http://www.starioninstruments.com/PDFs/Treat.pdf, downloaded Jun. 29, 2005, 2 pgs.
"Live Tissue Connect Technologies (Company Profile)", http://www.onemedplace.com/database/compdisplay_print.php?CompanyID=11508, (Oct. 19, 2010), 1 pg.
"Medical use of Radiofrequency (RF) Energy", http://www.locateadoc.com/Site_Tools/Print.cfm, (Aug. 23, 2008), 2 pgs.
"Everest Medical Announces Introduction of 3mm Bipolar Forceps", PR Newswire, 1002MNW021, (Oct. 2, 1996).
"Everest Medical Introduces new Quadripolar Cutting Forceps at the Global Congress for Gynecologic Endoscopy Meeting", PR Newswire, (Nov. 8, 1999), 8927.
"PKS Seal (Product Page)", http://www.gyrusacmi.com/user/display.cfm?display=product&pid=9024, 1 pg.
"Curon Medical Announces Presentation of Positive Clinical Study Results of STRETTA Procedure for Gastroesophageal Reflux Disease (GERD)", PR Newswire, NYW07920032002, (Mar. 20, 2002).
"Quadripolar Cutting Forceps Introduced by Everest Medical", Health Industry Today, vol. 63, No. 1 (Jan. 2000).
"The LigaSure Vessel Sealing System (Brochure)", TYCO Healthcare (Apr. 2002), 8 pgs.
"Everest Medical Discusses Patent Status: Forecasts $1 Million Revenue First Quarter: Introduces Next Generation Bipolar Scissors", (Mar. 31, 1994).
"Lyons Dissecting Forceps (Product Information)", GYRUS Medical, downloaded Oct. 5, 2005.
"2001 Hands-On Course I—Taking it the Next Level: Advanced Laparoscopic Techniques", http://www.sages.org/01program/syllabl/ho1.html#schirme, downloaded Oct. 5, 2005, 24 pgs.
"The Gynecare Versapoint (Product Information)", Johnson & Johnson Gateway, LLC, http://jnjgateway.com/home/jhtml?loc=USENG&page=viewContent&id=edea000100001747&parentid=fc0de00100000334, downloaded Oct. 20, 2005.
"Valleylab Products—Electrosurgical Forceps: The Surgeon's Choice for Quality and Precision (Product Information)", http://www.valleylab.com/products/es/accessories/forceps_over.html, downloaded Oct. 20, 2005.

(56) References Cited

OTHER PUBLICATIONS

"Micro/Macro-Jaw Forceps (Product Information)", GYRUS Medical, downloaded Oct. 5, 2005.
"2001 Nurses Program, Session 1 ", http://sages.org/01program/syllabi/nurse/nurse.html, downloaded Jan. 24, 2011, 5 pgs.
"Everest Medical Reports Record First Quarter Results: Introduces Next Generation Bipolar Scissors", PR Newswire, (Apr. 19, 1994).
"Cutting Forceps (Product Information)", GYRUS Medical, downloaded Oct. 5, 2005.
"Valleylab Products—Ligasure Vessel Sealing System (Product Information)", http://www.valleylab.com/product/vessel_seal/index.html, downloaded Oct. 20, 2005.
Aoki, "Thoracoscopic Resection of the Lung with the Ultrasonic Scalpel", Ann Thorac Surg, vol. 67, No. 4 (Apr. 1999),1181-1183.
Bergamaschi, "Laparoscopic Intracorporeal Bowel Resection with Ultrasound Versus Electrosurgical Dissection", JSLS, vol. 5, No. 1 (Jan.-Mar. 2001), 17-20.
Eichfeld, "Evaluation of Ultracision in Lung Metastatic Surgery", Ann Thorac Surg, vol. 70, No. 4 (Oct. 2000), 1181-1184.
Hayashi, "Experimental and Clinical Evaluation of the Harmonic Scalpel in Thoracic Surgery", Kurume Med J, vol. 46, No. 1 (1999), 25-29.
Hefni, "Safety and Efficacy of using the Ligasure Vessel Sealing System for Securing the Pedicles in Vaginal Hysterectomy: Randomized Controlled Trial", BJOG, vol. 112, No. 3 (Mar. 2005), 329-333.
Heniford, "Initial Results with an Electrothermal Bipolar Vessel Sealer", Surg Endosc, vol. 15, No. 8 (Aug. 2001), 799-801.
Kamat, "Superiority of Electrocautery Over the Suture Method for Achieving Cervical Cone Bed Hemostasis", Obstet Gynecol, vol. 102, No. 4 (Oct. 2003), 726-730.
Kennedy, "High-Burst-Strength, Feedback-Controlled Bipolar Vessel Sealing", Surg Endosc, vol. 12, No. 6 (Jun. 1998), 876-878.
Kim, "Design and Fabrication of a Locomotive Mechanism for Capsule-Type Endoscopes using Shape Memory Alloys (SMAs)", IEEE/ASME Trans on Mechatronics, vol. 10, No. 1 (Feb. 2005), 77-86.
Kovac, "Transvaginal Hysterectomy: Rationale and Surgical Approach", Obstet. Gynecol., vol. 103 (2004), 1321-1325.
Landman, "Evaluation of a Vessel Sealing System, Bipolar Electrosurgery, Harmonic Scalpel, . . . in a Porcine Model", J Urol, vol. 169, No. 2 (Feb. 2003), 697-700.
Levy, "Use of a New Vessel Ligation Device During Vaginal Hysterectomy (presentation abstract)", Presented at FIGO 2000, Washington D.C. (2000).
Levy, "Update on Hysterectomy: New Technology and Techniques", A Supp to OBG Management (Feb. 2003).
Lin, "Application of Ultrasonic Scalpel in Gynecologic Operative Laparoscopy", Chin Med J (Engl), vol. 114, No. 12 (Dec. 2001), 1283-1285.
Lyons , "An Innovative Bipolar Instrument for Laparoscopic Surgery", JSLS, vol. 9, No. 1 (Jan.-Mar. 2005), 39-41.
McClurken, "Collagen Shrinkage and Vessel Sealing", Technical Brief #300, Dover, NH, Tissue Link Medical (2001).
Nojarov, "High-Energy Scissors Mode", Phys Rev C Nucl Phys, vol. 51, No. 5, http://arxiv.org/abs/nucl-th/9502001v1, (1995), 2449-2456.
Parikh, "Three Dimensional Virtual Reality Model of the Normal Female Pelvic Floor", Annals of Biomedical Engineering, vol. 32 (Feb. 2004), 292-296.
Srisombut, "Laparoscopic Hysterectomy using Laparoscopic Coagulating Shears: Experience of 15 Cases", J. Med Assoc Thai, vol. 83, No. 8 (Aug. 2000), 915-920.
European Search Report issued in Application No. 11760294.6, dated Oct. 28, 2013.
Abu-Rustum, NR, et al., "Transperitoneal Laparoscopic Pelvic and Para-Aortic Lymph Node Dissection Using the Argon-Beam Coagulator and Monopolar Instruments: An 8-Year Study and Description of Technique," Jun. 2003; Gynecol Oncol. 89(3): 504-13; Memorial Sloan-Kettering Cancer Center, 1275 York Avenue, New York, NY 10021, USA, gynbreast@mskcc.org.

U.S. Appl. No. 12/410,322, Non-Final Office Action mailed Oct. 17, 2012.
Australian Examination Report for Application No. 2008214068, dated Jan. 28, 2011.
Australian Examination Report for Application No. 2008275543, dated Nov. 9, 2010.
Briani, S. et al.; Pseudo-Bipolar Electrocoagulation With a Branched Forceps; 1967; Minerva Neurochir.; 11 (3): 306-11.
Cakan. A. et al.: The Histological Effect of Harmonic Scalpel and Electrocautery in Lung Resections. An Experimental Study in a Rat Model: Feb. 2004; J Cardiovasc Surq (Torino).; 45 (1): 63-5; Department of Thoracic Surgery, Ege University School of Medicine, Izmir, Turkey, alpcakan@gohip.com.
Canadian Application No. 2,677,300, Examination Report mailed Apr. 18, 2013.
Canadian Application No. 2,723,016, Office Action mailed Nov. 12, 2013.
Canadian Examination Report for Application No. 2,677,300, dated Aug. 25, 2011.
Canadian Examination Report for Application No. 2,677,444, dated Aug. 18, 2011.
Ceviker. N. et al.; A New Coated Bipolar Coagulator: Technical Note; 1998; Acta Neurochir (Wien).; 140 (6): 619-20; Department of Neurosurgery, Faculty of Medicine, Gazi University, Ankara, Turkey.
Cherchi. PL. et al.: Utility of Bipolar Electrocautery Scissors for Cervical Conization: 2002; Eur J Gynaecol Oncol. 2002; 23 (2): 154-6; Department of Pharmacology, Gynecology and Obstetrics, University of Sassari, Italy.
Chinese Application No. 200880005429.2, Second Office Action mailed Mar. 6, 2013 with English translation.
Chinese Application Serial No. 200880005429.2, First Office Action mailed Aug. 20, 2012.
Chinese Application Serial No. 200880005613.7, Second Office Action mailed Jan. 31, 2013, 11 pgs. (English Translation).
Chinese Application Serial No. 200880005613.7, Third Office Action mailed Aug. 30, 2013.
Circon Corporation—Company Report; Investext, p. 1-13; Jan. 3, 1995.
Colvin. D.P. et al.: Development of an Endoscopic RF Hyperthermia System for Deep Tumor Therapy: 1987: American Society of Mechanical Engineers. Heat Transfer Division, (Publication) HTD v. 95. Publ by ASME (BED-v 7), New York, NY, USA p. 25-30.
Corson. S.L.: Two New Laparoscopic Instruments: Bipolar Sterilizing Forceps and Uterine Manipulator: Jan.-Feb. 1977; Medical Instrumentation vol. 11, No. 1 p. 7-8;; USA.
Daniel. P. et al.: Ultrasonic Sealing of the Lung Parenchyma After Atypical Resection: ZEXP Chir Transplant Kunstliche Organe. 1987: 20 (2): 117-21.
Digeronimo. EM et al.: Cut-Blot-Coagulate: A New Time Savino Device: Nov. 1982 Plast Reconstr Surg.; 70 (5): 639-40.
Dubuc-Lissoir. J.: Use of a New Energy-Based Vessel Ligation Device During Laparoscopic Gynecologic Oncologic Surgery: Mar. 2003 Surg Endosc.: 17 (3): 466-8.Epub Oct. 31, 2002; Department of Obstetrics and Gynecology, CHUM—Notre-Dame Hospital, Pavilion Charles-Simard, 2065 Alexandre-de-Seve, 4th Floor, Montreal, Quebec, Canada, H2L 2W5. josee.dubuc-lissoir.chum@ssss.gouv.qc.ca.
Entire patent prosecution history of U.S. Appl. No. 11/382,635, filed May 10, 2006, entitled, "Method for Tissue Cauterization," now U.S. Pat. No. 7,862,565, issued Jan. 4, 2011.
Entire patent prosecution history of U.S. Appl. No. 11/671,891, filed Feb. 6, 2007, entitled, "Electrocautery Method and Apparatus," now U.S. Pat. No. 8,696,662, issued Apr. 15, 2014.
Entire patent prosecution history of U.S. Appl. No. 11/671,911, filed Feb. 6, 2007, entitled, "Electrocautery Method and Apparatus," now U.S. Pat. No. 8,728,072, issued May 20, 2014.
Entire patent prosecution history of U.S. Appl. No. 12/062,516, filed Apr. 4, 2008, entitled, "Electrocautery Method and Apparatus."
Entire patent prosecution history of U.S. Appl. No. 12/121,734, filed May 15, 2008, entitled, "Electrocautery Method and Apparatus."
Entire patent prosecution history of U.S. Appl. No. 12/410,322, filed Mar. 24, 2009, entitled, "Electrocautery Method and Apparatus."

(56) References Cited

OTHER PUBLICATIONS

Entire patent prosecution history of U.S. Appl. No. 13/096,912, filed Apr. 28, 2011, entitled, "Apparatus for Tissue Cauterization," now U.S. Pat. No. 8,888,770, issued Nov. 18, 2014.
Ercoli. A. et al.: Radiofrequency Bipolar Coagulation for Radical Hysterectomy: Technique. Feasibility and Complications: Mar.-Apr. 2003 Int J Gynecol Cancer.: 13 (2):187-91 department of Obstetrics and Gynecology, Catholic University, Rome, Italy.
European Application Serial No. 08728715.7, European Examination Report dated Dec. 20, 2012.
European Patent Office Examination Report for Application No. EP 07 758 098.3 Dated Feb. 8, 2012.
European Search Report for Application No. PCT/US2008/052656 dated Mar. 30, 2012.
Everest Medical Releases Bicoag (TM) for Use in Treating Bleeding Ulcers: May 9, 1990:News Release, p. 1.
Examination Report for Canadian Application No. 2,677,300 dated Mar. 28, 2012.
Examination Report for Canadian Application No. 2,677,444 dated Jul. 3, 2012.
Examination Report issued in Japanese Patent Application No. 2012 173318, dispatched on Aug. 26, 2013.
Examining Report issued in corresponding Japanese Patent Application No. 2011 509759, dispatched on Aug. 6, 2013.
Final Office Action for U.S. Appl. No. 12/062,516 dated Jul. 27, 2012.
Forestier D. et al.: Do Bipolar Scissors Increase Postoperative Adhesions? An Experimental Double-Blind Randomized Trial: Nov. 2002, Ann Chir.; 127 (9): 680-4; Service de chirurgie generale et digestive, Hotel-Dieu, boulevard Leon-Malfreyt, 63058 Clermont-Ferrand, France.
Gerasin VA et al.: Endoscopic Electrosurgery of the Trachea and Bronchi; Sep.-Oct. 1988 Grudn Khir; (5): 50-3.
Gyr. T. et al.: Minimal Invasive Laparoscopic Hysterectomy With Ultrasonic Scalpel: Jun. 2001 Am J Surg.; 181 (6): 516-9; Department of Obstetrics and Gynecology, Regional Hospital, Lugano, Switzerland.
Harrell. AG et al.: Energy Sources in Laparoscopy: Sep. 2004 Semin Laparosc Surg.; 11 (3): 201-9; Carolinas Laparoscopic and Advanced Surgery Program, Carolinas Medical Center, Charlotte, NC 28203, USA.
Indian Examination Report issued in related Indian Application No. 2843/KOLNP/2009, dated Jul. 31, 2014.
Japanese Examination Report for Application No. 2009-549182, dated Oct. 27, 2011 with English translation.
Japanese Examination Report for Application No. 2009-549183, dated Oct. 27, 2011 with English translation.
Kato. K. et al.: A Computer Based. Temperature Controlled Bipolar Electrocoagulation System: Sep. 1996 Eur J Obstet Gynecol Reprod Biol.; 68 (1-2): 119-22; Department of Obstetrics and Gynecology, University of Essen, Germany.
Koss et al.; U.S. Appl. No. 12/907,646 entitled "Impedance Mediated Control of Power Delivery for Electrosurgery," filed Oct. 19, 2010.
Kung. RC et al: A New Bipolar System for Performing Operative Hysetroscopy in Normal Saline; Aug. 1999; 6 (3): 331-6J Am Assoc Gynecol Laparosc.http://www.ncbi.nlm.nih.gov/entrez/query.fcgi?cmd=Retrieve&db=pubmed&dopt=Abstract& list uids=10459037 &query hl=1.
Kwok. A. et al.: Comparison of Tissue Injury Between Laparosonic Coagulating Shears and Electrosurgical Scissors in the Sheep Model: Aug. 2001 J Am Assoc Gynecol Laparosc.; 8 (3): 378-84; Department of Endosurgery, Women's Institute, University of Sydney, Australia.
Lantis. JC II et al.: Comparison of Coagulation Modalities in Surgery: Dec. 1998 J Laparoendosc Adv Surg Tech A.; 8 (6): 381-94; Surgical Research Laboratory, New England Medical Center, Boston, Massachusetts, USA.
Laparoscopic Lasers Vs. Electrosurgery: Debated Technology Choices: Jun. 6. 1991: The BBI Newsletter, v. 14, n. 6, pN/A.

Market and Technology Updates: Bipolar Endoscopic Device: Jan. 24. 1990: The BBI Newsletter, v. 13, n. 1, pN/A.
Matsumura Y. et al.: New Surgical Technique of Pulmonary Segmentectomy by Ultrasonic Scalpel and Absorbable Sealing Materials: Jan. 2004 Kyobu Geka.: 57 (1): 31-7; Department of Thoracic Surgery, Institute of Development, Aging and Cancer, Tohoku University, Sendai, Japan.
Mundt. C. et al.: Advanced Sensor Systems for Improved Labor and Fetal Monitoring: 1998; ISA TECH/EXPO Technology Update Conference Proceedings v. 2 n. 2, p. 79-89; 1998.
Nikolov, N. et al.; Remote Controllable Vessel Occlusion Device: Jan. 1978 Med Biol Eng Comput.; 16 (1): 116-7.
Office Action for U.S. Appl. No. 12/062,516 mailed Mar. 16, 2015.
Ou. CS et al.: Total Laparoscopic Hysterectomy Using Multifunction Grasping. Coagulating, and Cutting Forceps: Apr. 2004 J Laparoendosc Adv Surg Tech A.; 14 (2): 67-71; Department of Research and Development, Northwest Hospital and University of Washington School of Medicine, Seattle, Washington 98155, USA. cou@nwhsea.org.
Pavlov. IUV et al.: Ultrasonic Technologies in Diagnosis and Treatment of Patients With Surgical Diseases of Lungs and Pleura; 2003 Khirurgiia (Mosk).; (8): 30-4.
Petrakis. IE et al.: Use of the Ligasure Vessel Sealer in Total Abdominal Hysterectomy: Jun. 2005 Int J Gynaecol Obstet.; 89 (3): 303-4. Epub Mar. 2, 2005; Department of General Surgery, University General Hospital of Heraklion, University of Crete, Heraklion, Crete, Greece, petrakis@post.com.
Raestrup. H. et al.: Dissection Technique Is Ultrasound the Best Method?: 2001 Kongressbd Dtsch Ges Chir Kohgr.; 118; 69-70; Universitatsklinik Fur Allgemeine Chirurgie, Hoppe-Seyler-Strasse 3, 72076 Tubingen.
Robinson JL et al.: Bipolar Diathermy: Sep. 1974 Can J Surg.;-17 (5): 287-91.
Stanojevic. D. et al.: An Ultrasonic Scalpel for Laparoscopic Gynecologic Surgery: May-Jun. 1998 Srp Arh Celok Lek.; 126 (5-6): 214-6; Narodni Front Department of Gynecology and Obstetrics, Dr. Dragisha Mishovitsh Medical Centre, Belgrade.
Sugi, K. et al.: Use of the Bipolar Vessel Sealing System in Lung Resection: Jul. 2003 Kyobu Geka.; 56 (7): 551-4; Department of Clinical Research, National Sanyo Hospital, Ube, Japan.
Tajiri M. et al.: Evaluation of an Ultrasonic Cutting and Coagulating System (Harmonic Scalpel) for Performing a Segmental and Wedge Resection of the Lung: Dec. 1998 Kyobu Geka.; 51 (13): 1116-9; Department of Surgery, Kan to Rosai Hospital, Kawasaki, Japan.
Tamussino. K. et al.: Electrosurgical Bipolar Vessel Sealing for Radical Abdominal Hysterectomy: Feb. 2005 Gynecol Oncol.: 96 (2): 320-2:Department of Obstetrics and Gynecology, Medical University of Graz, Auenbruggerplatz 14, A-8036 Graz, Austria. Karl. tamussino@meduni-graz.at.
Timor-Tritsch IE et al.: Transvaginal Ultrasound-Assisted Gynecologic Surgery: Evaluation of a New Device to Improve Safety of Intrauterine Surgery; Oct. 2003 Am J Obstet Gynecol.; 189 (4); 1074-9; Department of Obstetrics and Gynecology, New York University School of Medicine, NY 10016, USA. ilan.timor@med.nyu.edu.
Tucker. R.D. et al.: Capacitive Coupled Stray Currents During Laparoscopic and Endoscopic Electrosurgical Procedures: Jul.-Aug. 1992: Biomedical Instrumentation & Technology vol. 26, No. 4 p. 303-11;; USA.
Tucker. RD et al.: Bipolar Electrosurgical Sphincterotomv: Gastrointest Endosc. Mar.-Apr. 1992 ; 38 (2): 113-7; Department of Pathology, University of Iowa Hospitals Clinics, Iowa City 52242.
Valley Force Scientific Corp.—Company Report: Jan. 27. 1993: Investext. p. 1-1.
Weyl. BP: How to Increase the Proportion of Vaginal Hysterectomies-Bipolar Coagulation: Sep. 1999 Am J Obstet Gynecol.; 181 (3): 768.
Wilson. Fred: Cool Tool. Hot New Application: Radiofrequency Energy Removes Head, Neck Tumors. (Dermatologic Surgery): Aug. 2003; Dermatology Times, v. 24, n. 8, p. 54.

(56) References Cited

OTHER PUBLICATIONS

Zhi, Xu-Ting et al.; Management of Gastroesophageal Reflux Disease. Medications. Surgery. Or Endoscopic Therapy? (Current Status and Trends): 2005: Journal of Long-Term Effects of Medical Implants v. 15 n. 4 2005. p. 375-388g.

Koch. C. et al.: Determination of Temperature Elevation in Tissue During the Application of the Harmonic Scalpel; Feb. 2003 Ultrasound Med Biol.: 29 (2): 301-9: Ultrasonics Section, Physikalisch-Technische Bundesanstalt Braunschweig, Braunschweig, Germany. christian.koch@ptb.de.

Kohler C. et al.: Laparoscopic Coagulation of the Uterine Blood Supply in Laparoscopic-Assisted Vaginal Hysterectomy Is Associated With Less Blood Loss: 2004Eur J Gynaecol Oncol.; 25 (4): 453-6; Department of Gynecology, Friedrich Schiller University, Jena, Germany.

Office Action mailed Jun. 8, 2015 for U.S. Appl. No. 12/410,322.

Non-Final Office Action mailed Sep. 28, 2015 for U.S. Appl. No. 12/121,734.

Final Office Action dated Dec. 30, 2015 for U.S. Appl. No. 12/062,516.

\* cited by examiner

IMPEDANCE MEDIATED CONTROL OF POWER DELIVERY FOR ELECTROSURGERY

CROSS-REFERENCE TO RELATED APPLICATIONS

This application is a U.S. National Phase of PCT International Application No. PCT/US2011/029958 filed on Mar. 25, 2011, which claims the benefit of priority of U.S. application Ser. No. 12/907,646, now U.S. Pat. No. 8,827,992, filed on Oct. 19, 2010, which in turn is a continuation in part of U.S. application Ser. No. 12/748,229, now U.S. Pat. No. 8,419,727, filed on Mar. 26, 2010, the contents of all of the foregoing applications referred to in this paragraph being incorporated by reference herein for all purposes.

INCORPORATION BY REFERENCE

All publications and patent applications mentioned in this specification are herein incorporated by reference into the present application to the same extent as if each individual publication or patent application were indicated specifically and individually to be so incorporated.

FIELD OF THE INVENTION

The present disclosure relates to systems and methods for electrosurgical technology. More particularly, the technology relates to impedance-mediated control of power delivery for electrosurgical systems and methods for tissue sealing.

BACKGROUND

Biopolar electrosurgical instruments apply high radiofrequency (RF) electrical current to a surgical site to cut, ablate, or coagulate tissue. A particular application of these electrosurgical effects is to seal luminal structures, such as blood vessels or gastrointestinal sites, or tissue edges. A typical electrosurgical instrument takes the form of a pair of forceps, with electrodes positioned on both jaws of the forceps. In an electrosurgical procedure, the electrodes are placed in close proximity to each other as the jaws are closed on a target site such that the path of current between the two electrodes passes through tissue within the target site. The mechanical force exerted by the jaws and the electrical current combine to create the desired surgical effect.

By controlling the level of mechanical pressure applied by the jaws, the gap distance between electrodes, and the intensity, frequency, and duration of the electrosurgical energy applied to the tissue, a surgeon can coagulate, cauterize, or seal tissue toward a therapeutic end. A typical goal of controlling the delivery of electrosurgical energy, more particularly, is to apply no more and no less than the precise amount of energy required to create the desired effect within the targeted sealing site, while minimizing deleterious effects to tissue peripheral to the target site. As tissue absorbs energy, such as radiofrequency energy, its impedance of radiofrequency energy increases. This increase in impedance is generally considered to be a measure of the degree to which the tissue has been "processed" toward a therapeutic endpoint state. Embodiments of the presently disclosed systems and methods are directed toward using target tissue impedance as a feedback signal to appropriately control the level of energy applied to a targeted sealing site.

SUMMARY OF THE DISCLOSURE

Embodiments of the provided electrosurgical systems and methods include delivering energy from an electrosurgical device to a target tissue in a sealing cycle in the form of a series of pulses, each pulse being of a preset duration. The series of pulses begins with an initial pulse having a profile comprising a preset RF level start value that increases at a preset ramping rate to a preset RF end value. The methods may further include sending sensed tissue impedance values to a processor, or more specifically, to an impedance comparator element within a processor, throughout each pulse. Each pulse is either a preceding pulse to a subsequent pulse or a final pulse in a sealing cycle. The methods may further include comparing sensed impedance values to each of three preset impedance threshold values, including an impedance threshold value for RF setpoint, an impedance threshold value for cumulative time, and an impedance threshold value for energy cutback. The methods may further include controlling the delivery of energy during the sealing cycle by responding to the comparison of the sensed impedance values to the impedance threshold values.

In particular embodiments, controlling the delivery of energy includes ceasing the sealing cycle when the cumulative time of tissue showing an impedance value over the impedance cumulative time threshold value reaches a preset sealing cycle duration limit. Embodiments of the electrosurgical method may further include recording the cumulative time within an ongoing sealing cycle during which the sensed tissue impedance value exceeds the impedance threshold value for cumulative time.

Based on these comparisons of sensed impedance data to the impedance threshold values, various electrosurgical operating consequences may occur. When the sensed impedance value at the end of a preceding pulse is less than the impedance threshold value for RF setpoint, the methods may further include controlling the delivery of energy to the subsequent pulse such that it has substantially the same pulse profile as that of the initial pulse. When the sensed impedance value at the end of a preceding pulse exceeds the impedance threshold for RF setpoint, the methods may further include controlling the delivery of energy to the subsequent pulse such that it has an elevated profile. Such an elevated pulse profile may include stepping up at the outset of the pulse directly to the RF end value. An elevated pulse profile may also include ramping up from the RF start value to the RF end value at a rate greater than that of the preceding pulse.

When the sensed impedance at any time during a pulse exceeds the impedance threshold for energy cutback, the methods may include cutting back energy delivery. Such energy cutback may occur immediately, or it may include waiting for a preset elapsed amount of time to accumulate during which the sensed impedance exceeds the impedance threshold for energy cutback before cutting back energy delivery (up to about 2 seconds, for example).

Cutting back energy delivery may also include lowering any of an RF delivery level or a ramping rate. Lowering the amount of energy being delivered may include decreasing the energy delivery by an amount between about 1 and about 100 volts. Alternatively, lowering the amount of energy being delivered may include decreasing the energy delivery by a fractional percentage of that which is being delivered. More particularly, lowering the amount of energy being delivered may comprise decreasing the energy delivery by a fractional percentage of the amount of energy proportional to the extent to which the sensed impedance exceeds the impedance threshold for energy cutback value.

With regard to pulse duration and the RF values of pulses, in various embodiments of the electrosurgical method, the RF pulses, typically, are each of a constant duration that may range from about 0.5 sec to about 10 sec. The number of pulses in the series of pulses may range from 1 pulse to about 30 pulses. In various embodiments of the electrosurgical method, the cumulative sealing endpoint duration is between about 0.1 sec and about 5 sec. In various embodiments of the electrosurgical method, the RF start value is in the range of about 25 watts to about 150 watts, and the RF End Value is in the range of about 50 watts to about 150 watts.

With regard to the aforementioned impedance thresholds, in various embodiments of the method, the impedance threshold for RF setpoint is in the range of about 5 ohms to about 250 ohms, the impedance threshold for energy cutback value is in the range of about 100 ohms to about 900 ohms, and the impedance threshold for cumulative time value is in the range of about 100 ohms to about 750 ohms.

With regard to the transition from an RF start value to the RF end value of a pulse, in various embodiments of the electrosurgical method, delivering energy includes increasing the level of energy being delivered from the preset RF start value to a preset RF end value during a pulse. In some embodiments, increasing the level of energy during a pulse includes ramping up at a rate that ranges between about 1 watt/sec and about 100 watts/sec. In some embodiments, increasing the level of RF energy during a pulse includes ramping up in one or more steps. In some embodiments, increasing the level of energy during a pulse may include ramping up at a constant rate or at a changing rate. In still further embodiments, increasing the level of energy during a pulse comprises stepping up immediately to a preset RF end value upon initiation of a pulse.

In another aspect, an embodiment of an electrosurgical method includes delivering energy from an electrosurgical device to a target tissue site in a sealing cycle that includes a series of pulses, each pulse having a preset pulse duration. The series of pulses begins with an initial pulse having an initial pulse profile comprising a preset RF level start value that increases to a preset RF end value during the pulse. This embodiment of the method further includes sending a sensed tissue impedance value to a processor during each pulse, each pulse being either a preceding pulse to a subsequent pulse or being a final pulse. This latter embodiment of the method further includes controlling the delivery of energy during a sealing cycle such that: (A) a profile of a successor pulse relative to the profile of its preceding pulse has any of an identical profile or a higher energy profile, depending on a comparison of the impedance value shown by tissue during the initial or preceding pulse against a preset impedance threshold value for RF setpoint, (B) energy is cutback during a pulse when the sensed impedance value exceeds a preset threshold value for energy cutback; and (C) energy delivery ceases when a cumulative amount of time that sensed impedance has exceeded a preset impedance threshold value for cumulative time has accumulated a preset sealing cycle duration limit.

Further with regard to this latter embodiment of an electrosurgical method, when the sensed impedance exceeds the preset threshold value for RF set point, the energy profile of the succeeding pulse exceeds the energy profile of the preceding pulse, and when the sensed impedance is less than the preset threshold value for RF set point, the energy profile of the succeeding pulse is identical to the energy profile of the preceding pulse.

With respect to embodiments of an electrosurgical method, the energy profile of a pulse includes an RF start value, an RF end value, and a transition phase between the RF start value and the RF end value. In these embodiments, a lowered pulse energy profile of a successor pulse, with respect to the preceding pulse, may include any of a lowered RF start value, a lowered RF end value, and/or a lower rate of transition from the RF start value to the RF end value. A heightened energy pulse profile of a successor pulse, with respect to the preceding pulse, may include any of a higher RF start value, a higher RF end value, and/or a higher rate of transition from the RF start value to the RF end value. And finally, the transition from the RF start value to the RF end value comprises any of a sloped transition and/or a stepped transition.

DETAILED DESCRIPTION

The electrosurgical tissue sealing technology provided herein relates to applying the dynamics of the response of tissue to RF energy as feedback information to control the delivery of the energy during an electrosurgical procedure. Tissue sealing that is surgically optimal occurs when an appropriate level of energy is delivered to a target site at an optimal rate; too much energy, or energy delivered too quickly can damage the target site and surrounding tissue, and too little energy does not create a high integrity seal. Another consideration is that the effects of absorbing a given quantity of energy by a tissue sealing site is a function of the specifics of tissue type and total tissue volume receiving energy, both of which are variables at play in each sealing procedure. As tissue is being impacted or "processed" by RF energy, such as by coagulation, desiccation, or fulguration, or any combination thereof, impedance of the tissue to electrical current increases. The change in impedance is generally ascribed to a change in the "phase" or "state" of the tissue.

The relationship between energy input and the rate of change in the tissue state is affected by factors such as tissue composition, tissue density, water content, and electrolyte content. In these terms, an optimal rate of RF energy delivery is one that drives the change in tissue phase, as reflected in the rate of increase in impedance, at an optimal rate. The optimal rate of change in impedance can be learned empirically, from experimental and clinical experience. Accordingly, and as provided by embodiments of the method, the sensed change in tissue impedance during an electrosurgical procedure is an advantageous parameter to use as feedback in governing the rate of RF energy delivery to a targeted sealing site. A theoretical rationale of the method is offered to support of an understanding of its operation, but without any characterization that would limit claims to the method. It is considered advantageous to recognize when tissue is processing slowly, and, in response, to deliver energy to the tissue slowly. And, when tissue is processing quickly, in response, it is advantageous to deliver energy to the tissue quickly. The system is thus balanced so as to direct energy to a target site no more quickly than it can absorb the energy through tissue processing. Thus tissue is processed efficiently to an appropriate endpoint, and the spread of excess energy beyond the targeted tissue sealing site is minimized.

As described further below, impedance threshold values may be used to control the delivery of RF energy in a sealing cycle comprising a series of energy pulses delivered to a targeted tissue site. Sensed impedance may used to variously control energy delivery in real time, as during a pulse, or in a prospective manner, by controlling the delivery of energy in a succeeding pulse, as well as by terminating an energy delivery cycle at any point during a pulse.

Figure 1:
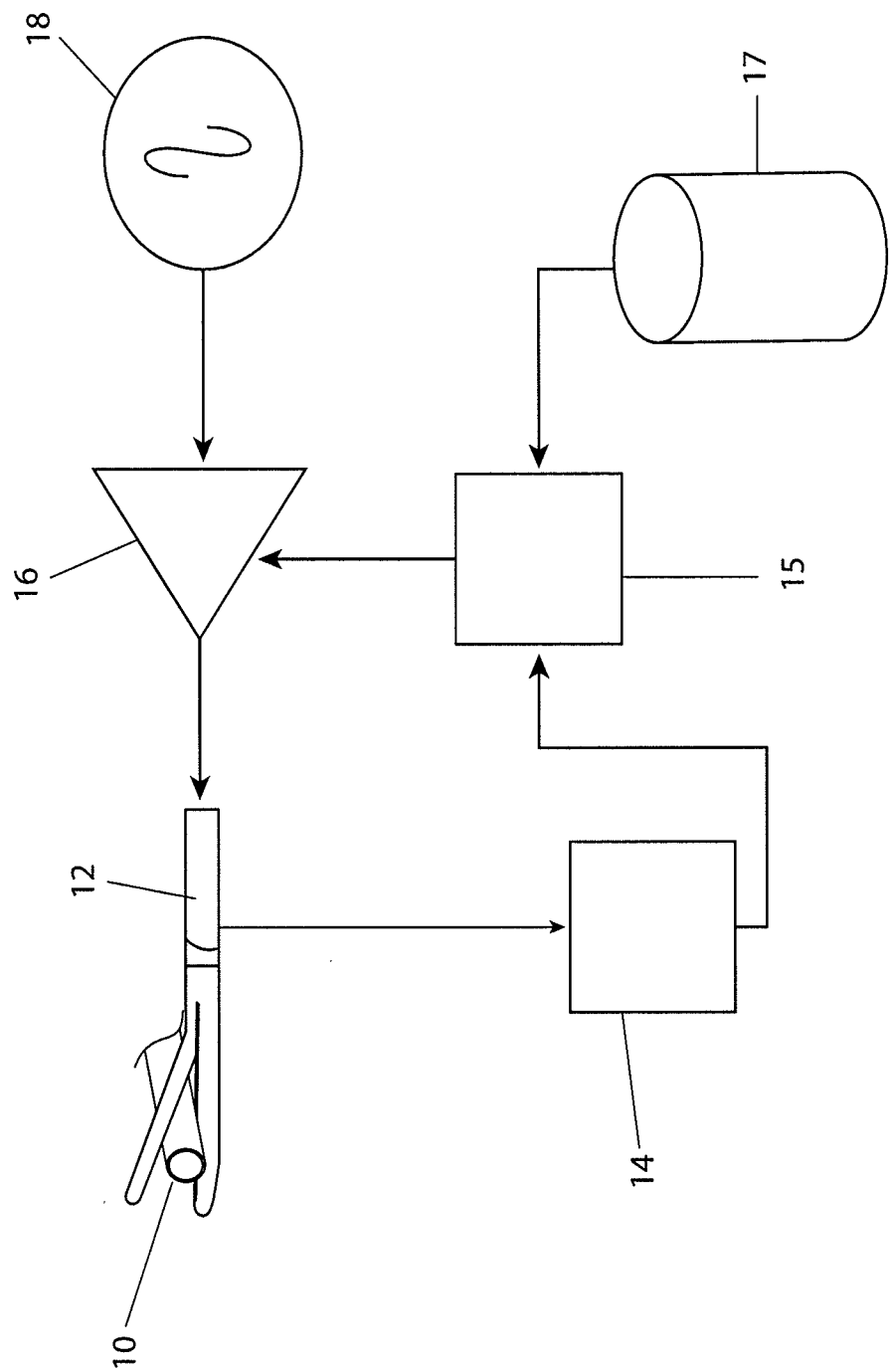
FIG. 1 is a block schematic diagram of a system for impedance-mediated RF power delivery for electrosurgery according to an embodiment of the disclosed technology.

FIG. 1 is a block schematic diagram of a system for impedance-mediated power delivery for electrosurgery according to the disclosed technology. Although the description, examples, and figures of the present disclosure relate primarily to aspects of a method for electrosurgical tissue sealing, embodiments of the technology also include a system and any subset of its components that are adapted or configured to operate per embodiments of the method. In FIG. 1, a procedure in which electrosurgery is being performed on the target tissue 10 of a patient by an electrosurgical device 12. A source of energy, such as a radiofrequency (RF) generator 18 is coupled to the electrosurgical appliance by a control circuit 16. In some embodiments, the control circuit is operable to adjust any of the current and voltage output and, thereby to adjust the power output of the RF generator. The control circuit can also adjust the RF generator output up or down in steps or it can ramp up or down at a selected slope during a pulse.

Embodiments of the method and systems for operating method embodiments provided herein are suitable for both single channel and multiple channel electrosurgical system operation. Multi-channel systems typically include an RF generator with multiple outputs coupled to multiple electrodes or electrode pairs. In multi-channel systems that make use of the embodiments of the method described herein, a generator may be capable of addressing electrodes individually and independently, such that electrode firing may occur without constraint with respect to repetition of individual electrode firing or with respect to the sequential order of adjacent electrode firing. In other words, the firing parameters of each electrode may be based on settings and/or feedback associated solely with that electrode.

The effect of the electrosurgical device on the tissue is monitored at the site of tissue treatment by one or more sensors associated with the electrosurgical appliance. A signal produced by the one or more sensors is coupled to a sensor circuit 14. The sensors can monitor environmental factors and operating parameters such as temperature, impedance, RF voltage, RF current, elapsed time, and the like. In particular embodiments, at least some of the sensors monitor the parameters of tissue impedance and RF power.

A sensor circuit 14 generates an output signal that is conveyed to a processor 15. The processor, operating under control of a program per aspects of the presently described method, is configured to adjust the output of the RF generator by issuing control signals to the control circuit. In doing so, the processor may adjust the RF power delivered to the tissue in real time, in response to signal generation by the sensors. The program may be retained in a memory 17 and includes both instructions for operating the processor and parameters that determine how to respond to signals from the sensor, timing, and other information as may be utilized to control the delivery of energy per aspects of the method.

As the tissue is processed by application of energy, a phase or state change occurs in the tissue that, in turn, causes a change in the impedance of the tissue. A particular feature of the provided technology is the manner in which the processor operates the control circuit and, thus, the manner in which energy is supplied to the tissue, in response to signals provided to the processor from one or more types of sensors, such as impedance sensors, via sensor circuitry.

More particularly, embodiments of the method apply sensed impedance to changing aspects of the profile of an electrosurgical pulse, components of a profile include an initial RF start value, an RF end value, and either a step-wise or ramped increase in RF delivery over the course of the pulse from the RF start value to the RF end value. As used herein, a "ramp" of energy output refers to the difference between the output level at the start of a pulse of energy delivery and the output level achieved at the end of the pulse, while "slope" refers more specifically to the rate at which the energy output changes over time during the pulse. Energy is typically delivered in a series of pulses that may be of a preselected or preset constant duration, although in some embodiments of the, the pulses may vary in length.

Embodiments of the electrosurgical system and method monitor the sensed impedance that target tissue manifests when being exposed to a pulse of RF energy and compares impedance data to various preset impedance threshold values during a sealing cycle that includes a series of pulses. Embodiments of the system and method respond to these comparisons by variously adjusting the profile of the ongoing pulse, adjusting the profile of the immediately succeeding or subsequent pulse, and by tracking time toward a cumulative sealing cycle endpoint duration, at which point the sealing cycle is terminated. These various system responses, collectively, represent a method for controlling aspects of the performance of an electrosurgical system during a sealing cycle, including the amount of power delivered during individual RF pulses, and during the sealing cycle as a whole.

Figure 2:
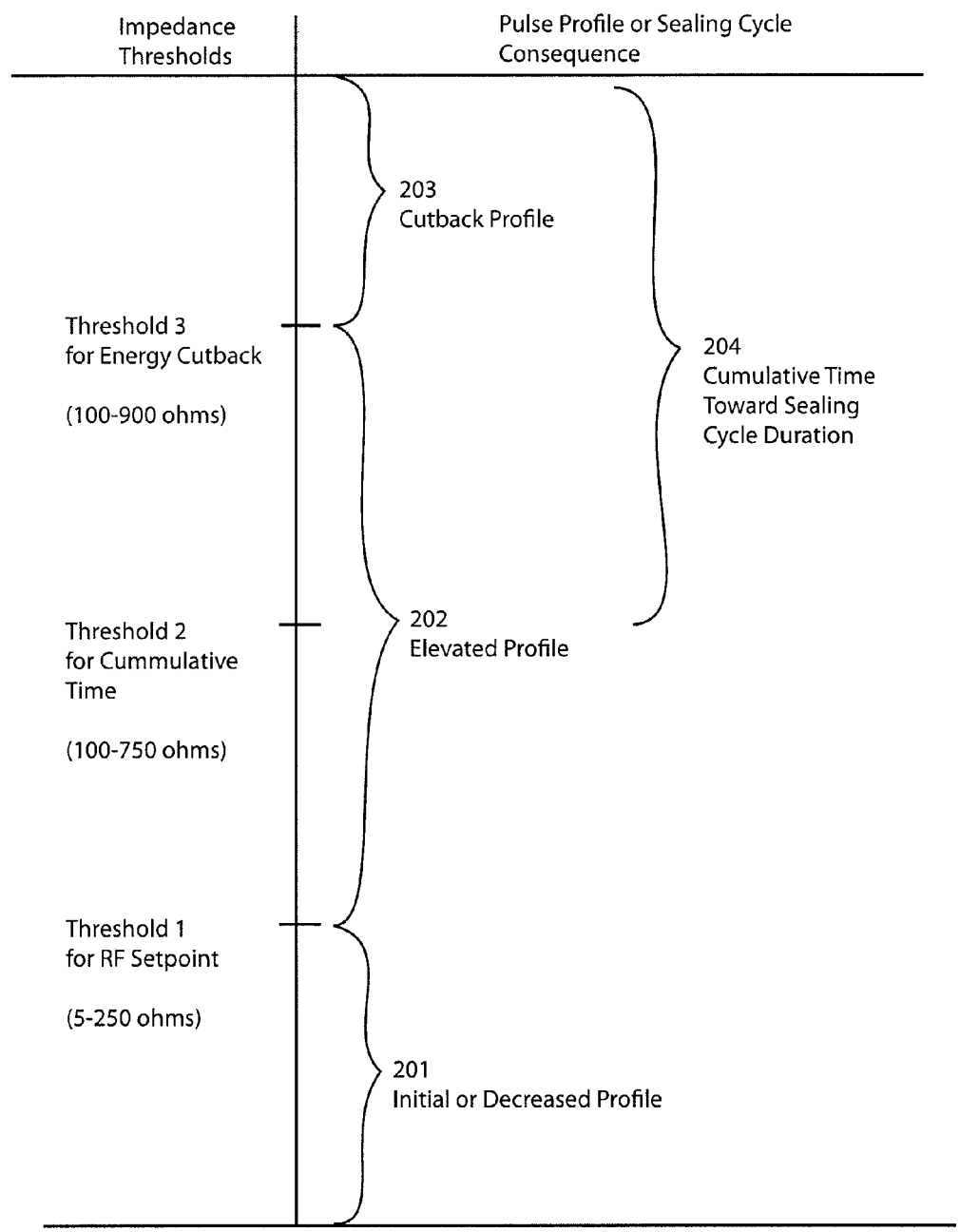
FIG. 2 is a schematic representation of impedance thresholds against which sensed impedance values may be compared and consequent responses with regard to RF energy delivery during an electrosurgical sealing cycle.
Figure 3:
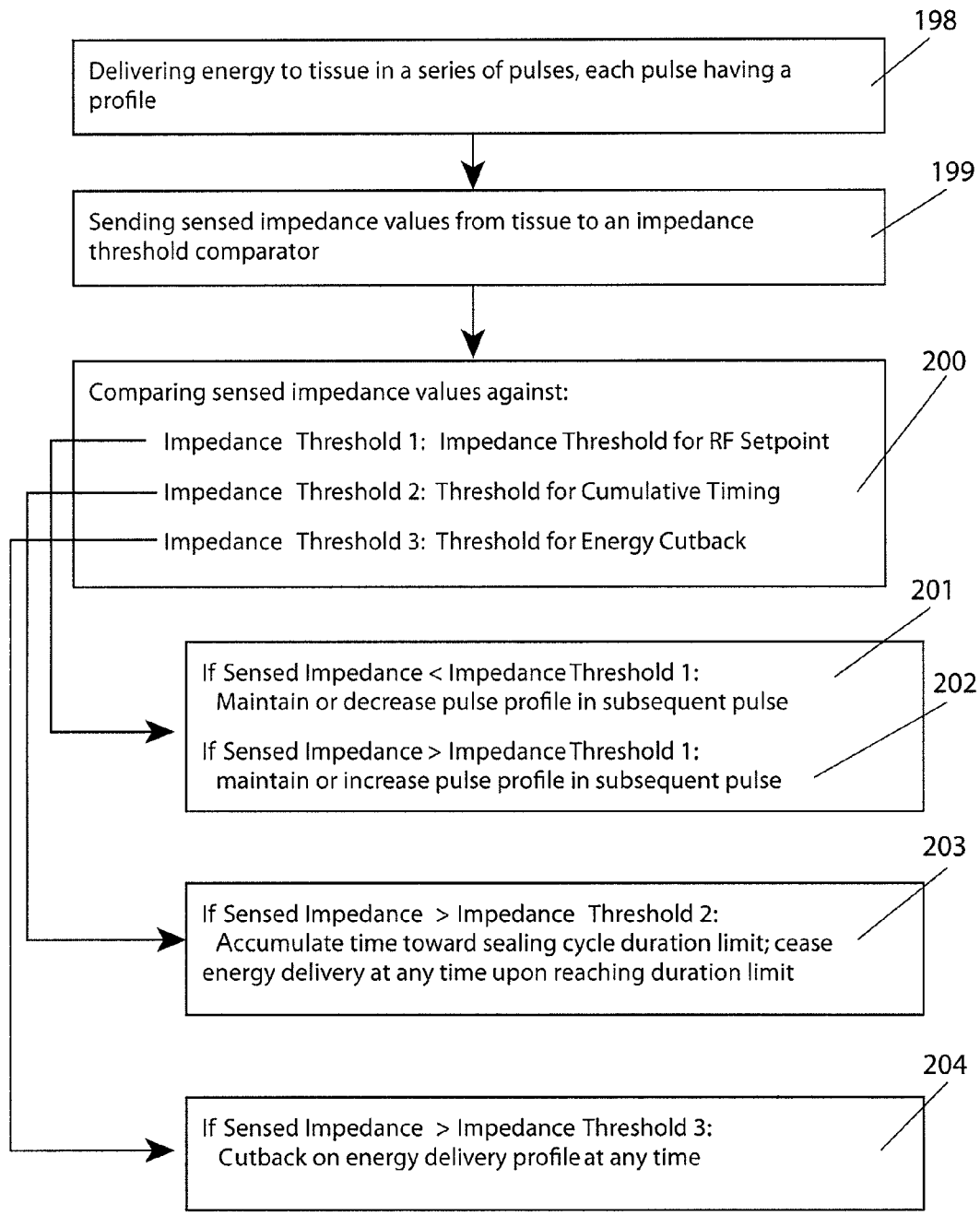
FIG. 3 is a flow diagram showing aspects of the disclosed method for using sensed impedance as feedback data to control delivery of RF energy during an electrosurgical sealing procedure.
Figure 4:
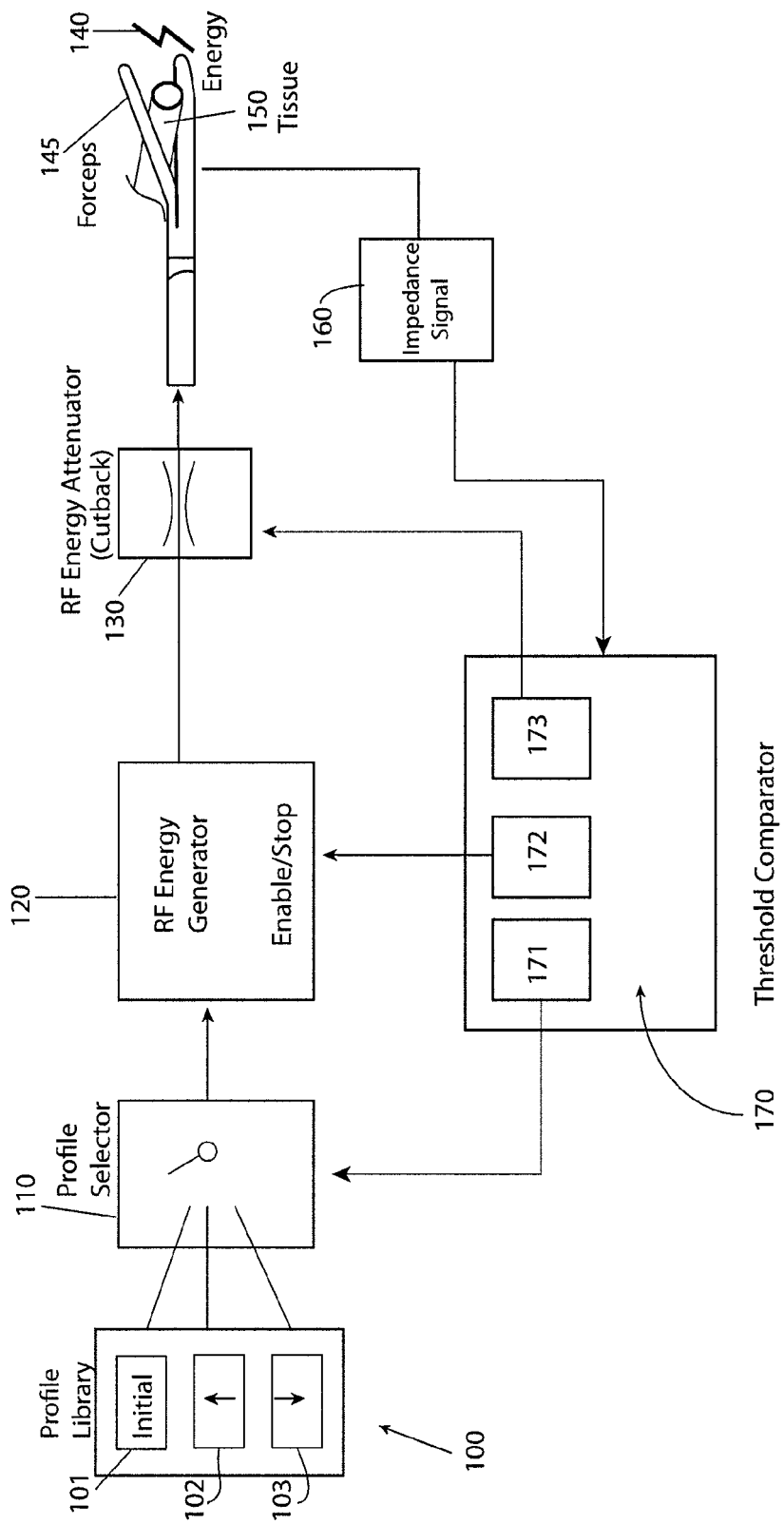
FIG. 4 is a flow diagram showing aspects of a system and method for using sensed impedance as feedback data to control delivery of RF energy during an electrosurgical sealing procedure.

These impedance threshold values include an impedance threshold value for an RF setpoint, an impedance threshold value for cumulative sealing cycle duration timing, and an impedance threshold value for energy cutback. Although the impedance values for each of these three threshold values include regions of overlap, the thresholds within typical embodiments of the method are ordered such that the impedance threshold value for an RF setpoint is the lowest threshold value, the impedance threshold for cumulative sealing cycle duration is the intermediate threshold value, and the impedance threshold value for energy cutback is the highest threshold value. These impedance threshold values and their roles in controlling energy delivery are detailed and described further below. Tables 1 and 2, as well as FIGS. 2, 3, and 4, provide overviews of aspects of the method, with particular attention to ways in which impedance data are fed back into the processor and used to control energy delivery to a targeted sealing site.

In one aspect, embodiments of the impedance-based power control method relate to controlling the profile of individual pulses within a series of pulses. Radiofrequency pulses, as delivered by embodiments of the method, have profile that includes a preset RF start value and a preset RF end value, typically higher than the RF start value. During the course of a pulse, the RF energy typically increases from the start value to the end value at a preset rate. In some pulses, per response to threshold impedance values as described further below, a pulse may step directly from the start value to the end value. Each of these parameters of a pulse profile is typically preset for a particular tissue sealing cycle, but each parameter may be adjustable within a range of values. The RF start value may range between about 25 and about 150 watts; a typical value, by way of example, is about 50 watts. The RF end value may range between about 50 and about 150 watts; a typical value, by way of example, is about 150 watts. The ramp rate or slope by which energy may increase from the RF start value to the RF end value may range between about 1 watt/sec and about 100 watts/sec; a typical value, by way of example, is about 50 watts/sec.

The impedance threshold value for RF setpoint is typically the lowest of the three impedance thresholds. This performance control mediating threshold has a preset value that ranges between about 5 and about 250 ohms; a typical value, by way of example, is about 50 ohms. Some embodiments of the system are configured to compare the tissue impedance at the conclusion of a pulse (or at its maximum) to this threshold value and to direct the profile of the succeeding pulse into one of two paths, depending on whether the pulse end impedance falls below or exceeds the RF setpoint threshold value. In the event that the end-pulse impedance (of a preceding pulse) is less than this threshold, the succeeding pulse is operated with the same profile as the preceding pulse.

In the event that the end-pulse impedance (of a preceding pulse) exceeds the impedance threshold value for RF setpoint, the succeeding pulse may be operated with a higher energy level profile. An elevated energy profile may occur by any approach that increases the integrated value of pulse duration multiplied by power; for example, in one embodiment, the pulse may initiate with the RF start value and then step directly (without an attenuated ramp) to the RF end value. In other embodiments, the slope of the energy delivery during the pulse may increase. In still other embodiments, the RF start value or the RF end value may be increased.

The impedance threshold value for cumulative sealing time duration is typically higher than the RF setpoint threshold value. In some embodiments, this performance control-mediating threshold has a preset value that ranges between about 100 ohms and about 750 ohms; a typical value, by way of example, is about 250 ohms. During the course of an electrosurgical procedure, as delivered by a series of pulses per aspects of the method, the impedance of target tissue increases. This increase is understood to be generally reflective of a tissue "processing" by RF energy to a level appropriate to serve a particular therapeutic end. Thus, the impedance shown by tissue may be considered a marker of tissue processing, and an optimal level of processing may be considered that rendered by absorbance of an optimal level of RF energy for an optimal duration of time. Accordingly, the system and method may be directed to record accumulated time at an impedance threshold value for cumulative time duration, which, upon being reached, causes the delivery of RF energy to cease. Cessation of energy delivery may occur immediately during an RF pulse upon accumulation of a preset sealing time duration. The cumulative sealing endpoint duration, per embodiments of the method, may range between about 0.1 sec and about 5 sec.

The impedance threshold value for energy cutback is typically the highest of the three impedance thresholds. This performance control-mediating threshold has a preset value that ranges between about 100 ohms and 900 ohms in some embodiments; a typical value, by way of example, is about 700 ohms. A high impedance level (see FIG. 8) reading during an RF pulse may be considered to be a consequence of low tissue presence in the electrosurgical space between the forceps of a device. It is, after all, tissue that is allowing conductance of RF energy between the forceps. In the complete absence of tissue, impedance within the circuit is absolute or infinite in practical terms. In the presence of low tissue, impedance is not infinite, but can quickly become very high. Low tissue presence may occur if, for example, tissue, or a portion thereof is particularly thin, compared to a typical amount of target tissue between the forceps. Or, there may be spaces between the forceps tips where tissue is simply absent. The electrosurgical system may respond to the high impedance event by cutting back on the level of energy delivery. Embodiments of the system thus include a timer that is configured to record the amount of time the tissue is manifesting this high impedance level, and upon accumulation of a preset amount of accumulated time, the system responds by cutting back on the amount of energy being delivered.

The energy cutback, per embodiments of the method, occurs by decreasing the profile of energy pulses being delivered. Such energy cutback may occur immediately, at any point during a pulse, when the impedance threshold for energy cutback is exceeded. In alternative embodiments of the method, energy cutback may occur after the passage of a preset delay. In still other embodiments, the energy cutback may be initiated in a succeeding pulse. The amount of energy cutback may occur by way of cutting back on level of energy delivery, or by way of decreasing the rate of energy increase during a pulse. Any one or more of several approaches may adjust the level of energy delivery downward. For example, the energy delivery may be dropped by an absolute amount of wattage or voltage. Alternatively, the level of energy delivery may be dropped by a fractional percentage of the level of energy being delivered at the moment when the impedance threshold for energy cutback is exceeded. In another variation, the level of energy delivery may be dropped by the fractional portion that corresponds to the difference between the sensed impedance and the impedance threshold for RF energy cutback. It can be noted, merely for the purpose of understanding the rationale of aspects of the method, that an exceptionally fast increase in impedance which includes exceeding the impedance threshold for energy cutback is indicative of a small amount of tissue, rather than a normal amount of tissue, absorbing all of the delivered energy, and thus being processed more quickly than is desired.

FIG. 2 provides a schematic outline of the three impedance thresholds used in aspects of the method to control the delivery of energy during an electrosurgical procedure, and consequences that follow from sensed impedance data being delivered back to system components that control the delivery of energy. The impedance thresholds are arranged on the left side of the figure, aligned against an axis of ascending ohm values. Impedance threshold 1 pertains to the RF setpoint, impedance threshold 2 relates to cumulative time, and impedance threshold 3 relates to energy cutback. The right side of the figure shows the energy delivery consequences to impedance values sensed during a pulse, as they fall into ranges bracketed by these thresholds. These energy delivery consequences pertain either to a pulse following the preceding pulse (during which time the sensed impedance occurred) or to immediate, real-time, consequences to energy delivery during the pulse.

Continuing with FIG. 2, starting with the lowest threshold, the impedance threshold for RF setpoint, the bracketed segment 201 on the right side of the figure shows that a sensed impedance value (typically the impedance at the conclusion of a time pulse) that falls at or below this threshold causes the profile of energy delivery in the subsequent pulse to remain the same or be decreased. Such decrease may be a one-time event, after which the profile remains constant, or such decrease may continue with each successive pulse. As noted above, a profile may decrease either by way of downward adjustment of RF setpoints, or by diminishing the rate by which RF energy increases during the pulse.

Continuing with FIG. 2, ascending from the lowest bracketed segment 201, the next bracketed segment 202 extends upward from the impedance for RF setpoint to the impedance threshold for energy cutback. The right side of the figure notes that the profile of the energy pulse that follows a preceding pulse where the sensed impedance (typically the impedance at the conclusion of a time pulse) has fallen into this segment is delivered with an elevated profile. Such increase may be a one-time event, thereafter which the profile remains constant, or such increase may continue with each successive pulse. As noted above, a profile may increase either by way of upward adjustment of RF setpoints, or by increasing the rate by which RF energy increases during the pulse.

Continuing further with FIG. 2, a bracketed segment 203 extends above the threshold for energy cutback toward maximal impedance. The consequence of a sensed impedance value occurring at any point during a pulse falling into this bracketed range is that energy delivery is cutback, while the pulse is ongoing. In some embodiments, energy is cutback immediately; in other embodiments, energy is cutback after a delay of up to seconds. This delay, if implemented, is for the purpose of validating that the high impedance event is real and sustaining, not due to a transient or erroneous signal from an impedance sensor.

Finally, with regard to FIG. 2, a large bracketed segment 204 embraces sensed impedance values that range upward from the impedance threshold for cumulative time. As sensed impedance values rise above this threshold, a timer is initiated that runs as long as impedance is above this threshold value. If impedance falls below this threshold value, as it may when energy is cutback, the timer ceases accumulating time. As impedance then may rise again to surpass the threshold, the timer again accumulates time. Upon the accumulation of a preset cumulative time duration for the sealing cycle, energy delivery during the cycle ceases.

FIG. 3 is a flow diagram that shows elements of a method for using sensed impedance as feedback data to control delivery of RF energy during an electrosurgical sealing procedure. In an initial step 198, energy is delivered to a target tissue site in a series of pulses, each pulse having a profile that may or may not be adjusted in response to sensed impedance data in the subsequent pulse. In a second step 199, sensed impedance data are sent to an impedance threshold comparator within the system. In a third step 200, sensed impedance data are compared to an impedance threshold (1) for the RF setpoint, an impedance threshold (2) for cumulative timing of the preset sealing cycle duration, and (3) an impedance threshold (3) for energy cutback at any time during a pulse.

As a result of these comparisons ongoing within the comparator (FIG. 3), any one of several consequences may follow. In the event 201 that sensed impedance is less than impedance threshold 1, the profile of the subsequent pulse is either maintained or decreased. In the event 202 that sensed impedance is greater than impedance threshold 1, the profile of the subsequent pulse is either maintained or increased. In the event 203 that sensed impedance is greater than impedance threshold 2, a cumulative timing function is initiated, which accumulates time toward a preset sealing cycle duration. When such time reaches the preset sealing cycle duration, energy delivery ceases immediately. In the event 204 that sensed impedance is greater than impedance threshold 3, energy delivery is cutback either immediately during the instant pulse, or cutback after a short delay to serve the purpose of validating the high impedance incident.

FIG. 4 is a flow diagram showing aspects of a method and system for using sensed impedance as feedback data to control delivery of RF energy during an electrosurgical sealing procedure. Aspects of the method draw upon a library and adjuster 100 of RF pulse profiles that includes an initial profile 101, an elevated profile 102, and a lowered profile 103. The initial profile is preset; the values of parameters RF start value, RF end value, and the transition between the them (slope or step) can all vary within their respective ranges, as shown in Table 1. The parameters of the lowered and elevated profiles also vary per the ranges of Table 1, with the qualification that the profiles as a whole, are either lower or higher, respectively, than the parameters of the initial pulse profile 101.

Prior to the delivery of an RF pulse, an RF pulse selector 110 selects which pulse profile in the profile library (101, 102, or 103) to deliver to tissue 150. The pulse selector 110 makes the selection based on input from a threshold comparator 170 (see further, below). The RF pulse selector 110 has an output that drives the setpoint for the RF energy generator 120, which delivers an RF energy pulse 140 that is ultimately directed to a target tissue site 150. As energy is being delivered it passes through an intervening mechanism in the form of an RF energy attenuator or cutback block 130 that can attenuate the energy delivery, in real time, based on data from the threshold comparator 170.

The target tissue site 150 is both the recipient of RF energy 140 being delivered by the system via electrosurgical forceps 145, as well as the source for impedance data 160 that are conveyed back to the system, stored in a memory and processed by a processor, as represented by a threshold comparator 170. The threshold comparator performs constant surveillance of sensed impedance data from the target tissue and compares these data against three particular impedance thresholds, as outlined in FIG. 2, and as described further below in an outlined summary of an embodiment of the method.

Briefly, these impedance thresholds include an impedance threshold for the RF setpoint 171, an impedance threshold for pulse duration cumulative timing 172, and an impedance threshold for energy cutback 173. It can be seen that the result of a comparison 171 of impedance data with respect to an RF setpoint threshold value is directed into the profile selector and adjuster 110, which then typically assigns either an elevated profile 102 or a lowered profile 103 for the subsequent pulse in response to the incoming data. The result of the comparison 172 of impedance data with respect to an impedance threshold for cumulative time is directed to the RF energy generator/delivery block 120; if the cumulative time is less than the preset duration, block 120 is enabled to generate RF energy. When the cumulative time achieves the preset sealing cycle duration, further delivery of energy from block 120 is stopped. The result of the comparison of impedance data with respect to an impedance threshold of energy cutback 173 is directed into the RF energy attenuator cutback block 130. If data from impedance comparison 173 indicates that the impedance is less than the impedance threshold for energy cutback, energy delivery proceeds without attenuation. If data from impedance comparison 173 indicates that the impedance exceeds the impedance threshold for energy cutback, energy delivery proceeds with attenuation in real time.

In some embodiments, in response to tissue impedance exceeding the impedance threshold for energy cutback, energy is cutback by an amount proportionate to the total amount of energy being delivered during the high impedance event. The fractional amount by which energy is cutback, in some embodiments, may be related to the proportional amount by which the sensed impedance is exceeding the impedance threshold for energy cutback. For example, if the impedance threshold for energy cutback is 300 ohms and sensed impedance is 450 ohms (50% greater than the impedance threshold of 300 ohms), the energy delivery may be cutback by 50%. In some embodiments of this proportional energy cutback procedure, the cutback is performed in a continuous real time manner, with the response to energy cutback immediately tracking the extent to which sensed impedance exceeds the threshold for energy cutback.

Table 1 summarizes the values of various parameters associated with the delivery of radiofrequency energy and the sensed target tissue impedance during an electrosurgical tissue sealing procedure, in accordance with aspects of the disclosed methods. The specific value drawn from within range (for RF values and impedance thresholds) is typically preset and fixed for any given electrosurgical procedure, however these preset values are adjustable within the range.

TABLE 1

Radiofrequency Sealing Method Parameters

| Parameter | Example | Typical Range |
|---|---|---|
| RF Pulse Time Parameters | | |
| RF Pulse Duration | 3.0 sec. | 0.5-10.0 sec. |
| Max RF Pulse Count per sealing event | 5 pulses | 1-30 pulses |
| Cumulative Sealing Endpoint Duration Limit (total time when impedance exceeds endpoint timing threshold) | 1.5 sec. | 0.1-5.0 secs. |
| RF Levels and Ramping Rate | | |
| RF Start Value, initiating a pulse | 50 watts | 25-150 watt |
| RF End Value, at the end of a pulse | 150 watts | 50-150 watt |
| RF Ramp Rate (or slope) during a pulse | 50 watt/sec. | 1-100 watt/sec. |
| Tissue Impedance Parameters | | |
| Pulse-end Impedance | the tissue response | 2-900 ohms |
| Impedance Threshold (1) for RF Setpoint (determining energy parameters of next pulse) | 50 ohms | 5-250 ohms |
| Impedance Threshold (2) for Cumulative Time (cumulative time above this value contributes to cumulative sealing endpoint duration) Energy cutback in response to a high impedance event | 250 ohms | 100-750 ohms |
| Impedance Threshold (3) for Energy Cutback | 300 ohms | 100-900 ohms |

TABLE 1-continued

Radiofrequency Sealing Method Parameters

| Parameter | Example | Typical Range |
|---|---|---|
| Energy Cutback Time | 0.1 sec. | 0-2.0 secs |
| Energy Cutback Fraction (Cut energy delivery back to a fractional portion of the energy being delivered at the point when the impedance threshold is exceeded.) | 50% | Cutback energy by 10%-90% (to a level between 90% and 10% of pre-cutback) |

Table 2 summarizes the profile of the RF pulse that follows a preceding pulse, as controlled by the sensed tissue impedance during the preceding pulse, as well as other system responses to sensed impedance values during an exemplary sealing cycle.

TABLE 2

Subsequent Energy Delivery and Sealing Cycle Endpoint Consequences to Sensed Tissue Impedance Response During Energy Delivery

| Profile of the Initial or Preceding RF pulse | Sensed Tissue Impedance During RF Pulse | Consequences re Continued Energy Delivery and Cumulative Timing toward Cycle Stop |
|---|---|---|
| The RF start value is at a preset initial value; it ramps up at a preset rate to a preset RF end value | A sensed end-pulse impedance value that is less than impedance threshold (1) for RF setpoint | In the succeeding pulse, maintain same profile as that of the preceding pulse |
| | A sensed end-pulse impedance value that exceeds impedance threshold (1) for RF setpoint | In the succeeding pulse, step up immediately to the RF end value. |
| | A sensed impedance value at any time during a pulse that exceeds impedance threshold (2) for cumulative timing duration | A timer tracks the cumulative time toward a sealing endpoint time duration which; when that duration is reached, the sealing cycle stops |
| | A sensed impedance value at any time during a pulse that exceeds impedance threshold (3) for energy cutback, indicative of low tissue presence | Cutback of RF energy delivery at any time during the cycle. If sensed impedance value again exceeds impedance threshold (3), repeat cutback. In some embodiments, the cutback is proportional to the amount of energy being delivered, and operates in a continuous real time manner. |

An embodiment of the method by which sensed impedance controls the delivery of RF energy during an electrosurgical tissue sealing cycle is summarized below.

1. Initiate a sealing cycle with a pulse at a preset initial RF Start Value; ramp up power at a preset initial RF ramp rate during the pulse until power reaches an RF End Value; continue at that power level for duration of a preset pulse duration, and then cease energy delivery to conclude the pulse.
2. Obtain sensed tissue impedance data continuously throughout the RF initial pulse and every subsequent pulse. All of the sensed impedance data are stored in a memory to which a processor has access. In various aspects of the method, sensed impedance data from any point during the pulse may be used as a value to compare to any one or more of three impedance threshold values. In some aspects of the method, the sensed impedance at the end of a pulse is a particular value used in comparison to impedance threshold values.

3. Continuously compare the sensed impedance values from all points during a pulse with respect to (a) an impedance RF setpoint threshold value, (b) an impedance threshold for cumulative timing threshold, and (c) an impedance energy-cutback threshold value. Take the sealing cycle forward in accordance with the following options (4A, 4B, 4C, or 4D), depending on the result of these comparisons.

4A. If, at the end of a preceding pulse, the sensed pulse end impedance value is less than the impedance threshold for RF Setpoint value, deliver energy during the subsequent pulse with a pulse profile substantially identical to that of the preceding pulse. The sealing cycle proceeds in this manner until a preset sealing time duration is achieved, as in 4C.

4B. If, at the end of a pulse, the sensed pulse-end impedance value is greater than the impedance threshold for RF Setpoint value, deliver energy during the subsequent pulse with a pulse profile higher than that of the preceding pulse. In some embodiments of the method, this increase in pulse profile occurs just once, during the pulse that follows the initial pulse. In some embodiments of the method, the pulse profile is increased by undergoing an immediate step up from the RF start value to the RF end value (rather than by way of a ramping increase, as typical of the initial pulse). The sealing cycle proceeds in this manner until a preset sealing time duration is achieved, as in 4C.

4C. If, at any time during any pulse, the sensed impedance exceeds an impedance threshold for cumulative sealing time, a timer is initiated that runs for a preset sealing time duration. If sensed impedance falls below this threshold, the cumulative timer stops recording time. Upon completion of the preset sealing time duration, delivery of energy ceases, thus concluding the sealing cycle.

4D. If, at any time during any pulse, the tissue impedance value exceeds the impedance threshold for energy-cutback threshold value, the level of energy being delivered is cutback. In some embodiments, the energy is cutback immediately; in other embodiments the energy is cut back following the passage of a preset energy cutback time. Following the energy cutback, the sealing cycle proceeds until either the impedance threshold for energy cutback is exceeded again (in which case, energy is cutback again), or until the preset sealing duration time is achieved, as in 4C, whereupon the delivery of energy ceases.

Figure 5:
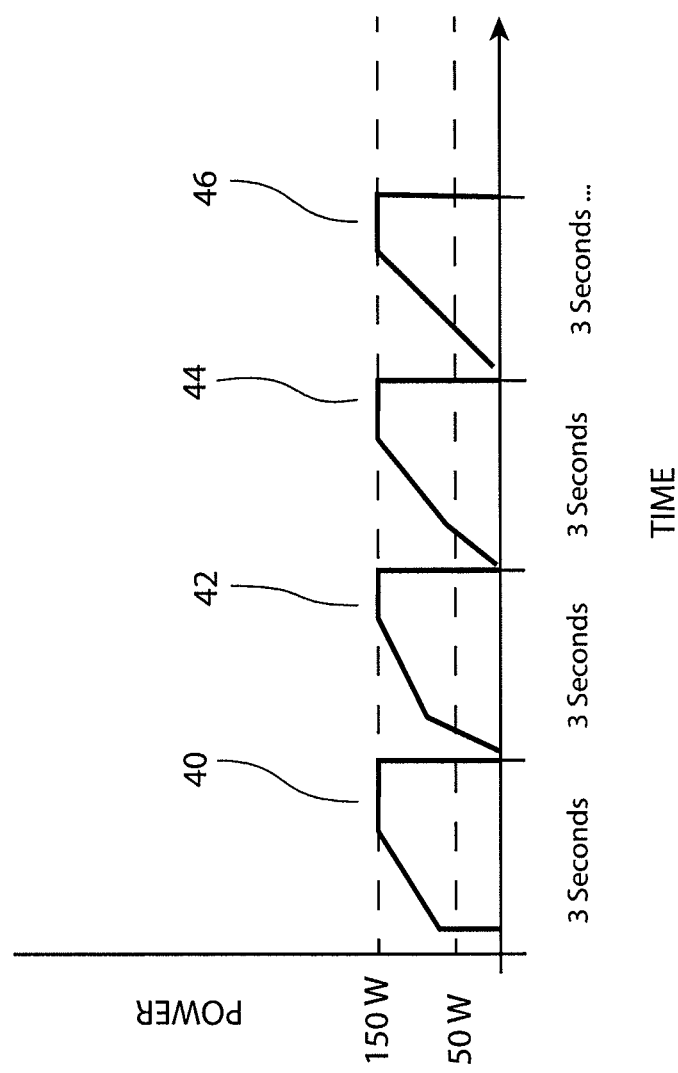
FIG. 5 is a timing diagram showing an example of impedance-mediated control of a power delivery ramp for electrosurgery according to an embodiment of the method.

FIGS. 5-8 provide examples and demonstrations of aspects of the electrosurgical tissue sealing method provided herein. FIG. 5 is a timing diagram showing an example of an impedance-mediated power delivery ramp as it occurs in a series of four pulses (40, 42, 44, and 46), each of which is preset to be 3 seconds in duration. As seen in Table 1, the length of the pulse intervals may be preset to vary from this 3-second duration within a range of about 0.5 sec to about 10 sec. In this present example of the method, the pulses (or pulse intervals) are all equivalent in duration. In alternative embodiments of the method, the pulse duration or intervals may also vary in length from one to another, either by a preset schedule or in response to a comparison of sensed impedance values against impedance threshold values during a sealing cycle. When pulses are of a varying duration during a sealing cycle, they may be preset to either increase or decrease in length through the cycle, or they may increase or decrease in any preset pattern. When pulse length varies in response to sensed impedance values, the length may increase or decrease in any pattern.

In the example provided by FIG. 5, the total amount of energy being delivered is decreasing with each successive pulse. The slope of the first ramp interval 40 includes a first, steep portion, a shallow middle portion, and a substantially flat third portion. Upon the conclusion of the pulse, the energy is reduced and the next ramp is initiated. In this embodiment of the method, the slope of each ramp is adjusted in real time, in response to the rate of change of tissue impedance during the preceding pulse. The slope of the second ramp 42 includes an initial portion that is shallower than that of first ramp 40; and the slope of the third ramp 44 is shallower than the initial portion of ramp 42 preceding it; and the initial slope of the fourth ramp 46 is even more shallow. The area under each ramp indicates the total energy supplied to the tissue during the ramp. Thus, in this example, a decreasing amount of energy is applied during each successive pulse. In other embodiments of the system and method, the ramped RF values and the slope between them may be varied independently in response to sensed impedance values. This pattern of a gradual decrease in energy being delivered in each pulse, following by a leveling off energy delivery is typical of an electrosurgical sealing cycle in which the sensed impedance is falling below the impedance threshold for the RF setpoint.

Figure 6:
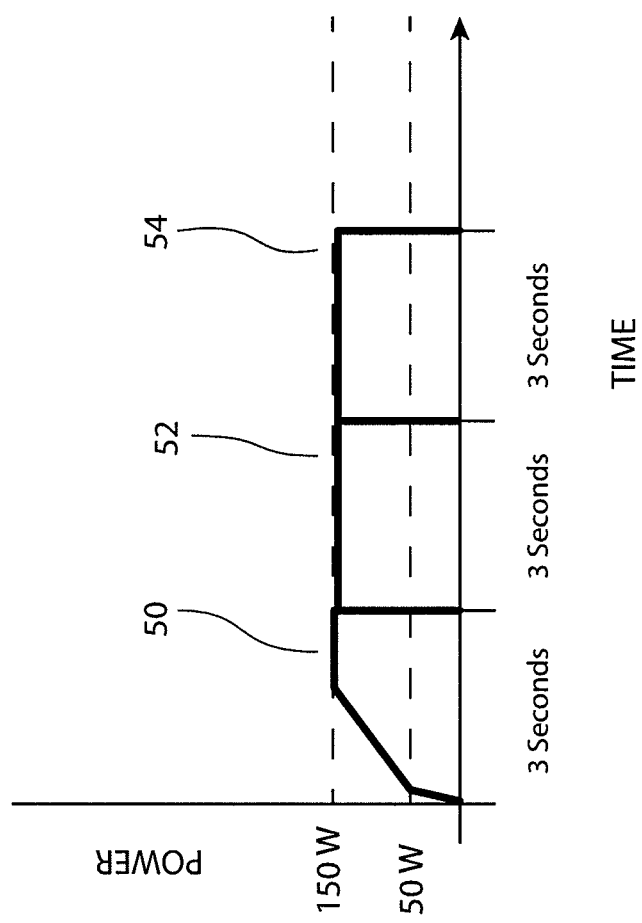
FIG. 6 is a timing diagram showing an alternative example of impedance-mediated control of power delivery interval for electrosurgery according to an embodiment of the method.

FIG. 6 is another timing diagram showing an example of an impedance-mediated energy delivery ramp as it occurs in a series of three pulses (50, 52, and 54) being operated according to an aspect of the method. In FIG. 5, an initial energy ramp 50 is supplied to the tissue. In this case, in response to tissue impedance readings and comparison to impedance threshold values, an increase in pulse profile subsequent to the initial pulse is provided. Once the desired impedance is reached, the energy supplied to the tissue at pulses 52 and 54 is maintained at a desired level for a predetermined interval of time. This pattern of a gradual increase in energy being delivered in each pulse, following by a leveling off energy delivery is typical of an electrosurgical sealing cycle in which the sensed impedance is exceeding the impedance threshold for the RF setpoint.

Figure 7A:
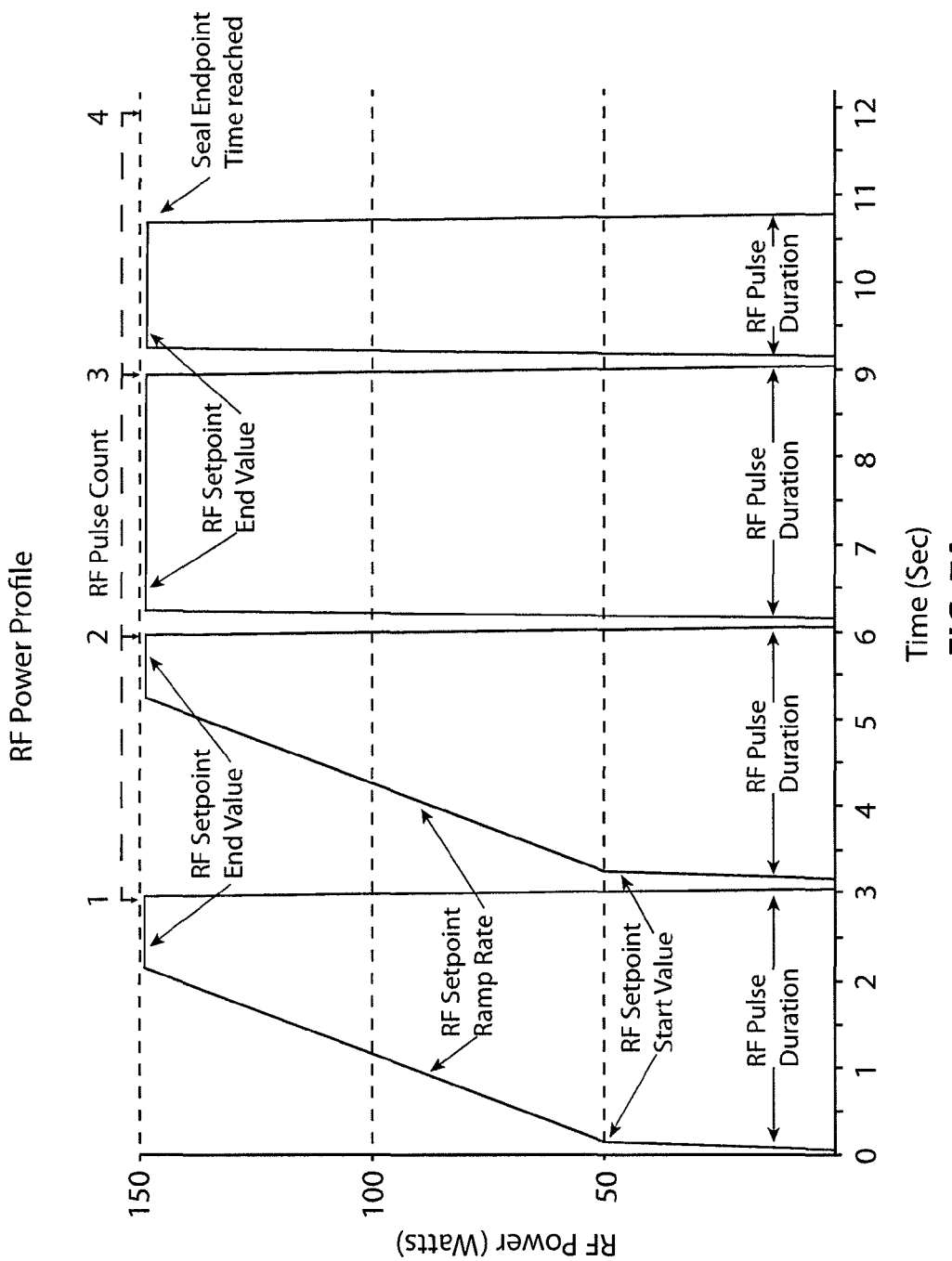
FIG. 7A is a timing diagram showing an RF power delivery profile as controlled by tissue impedance feedback according to an embodiment of the method.
Figure 7B:
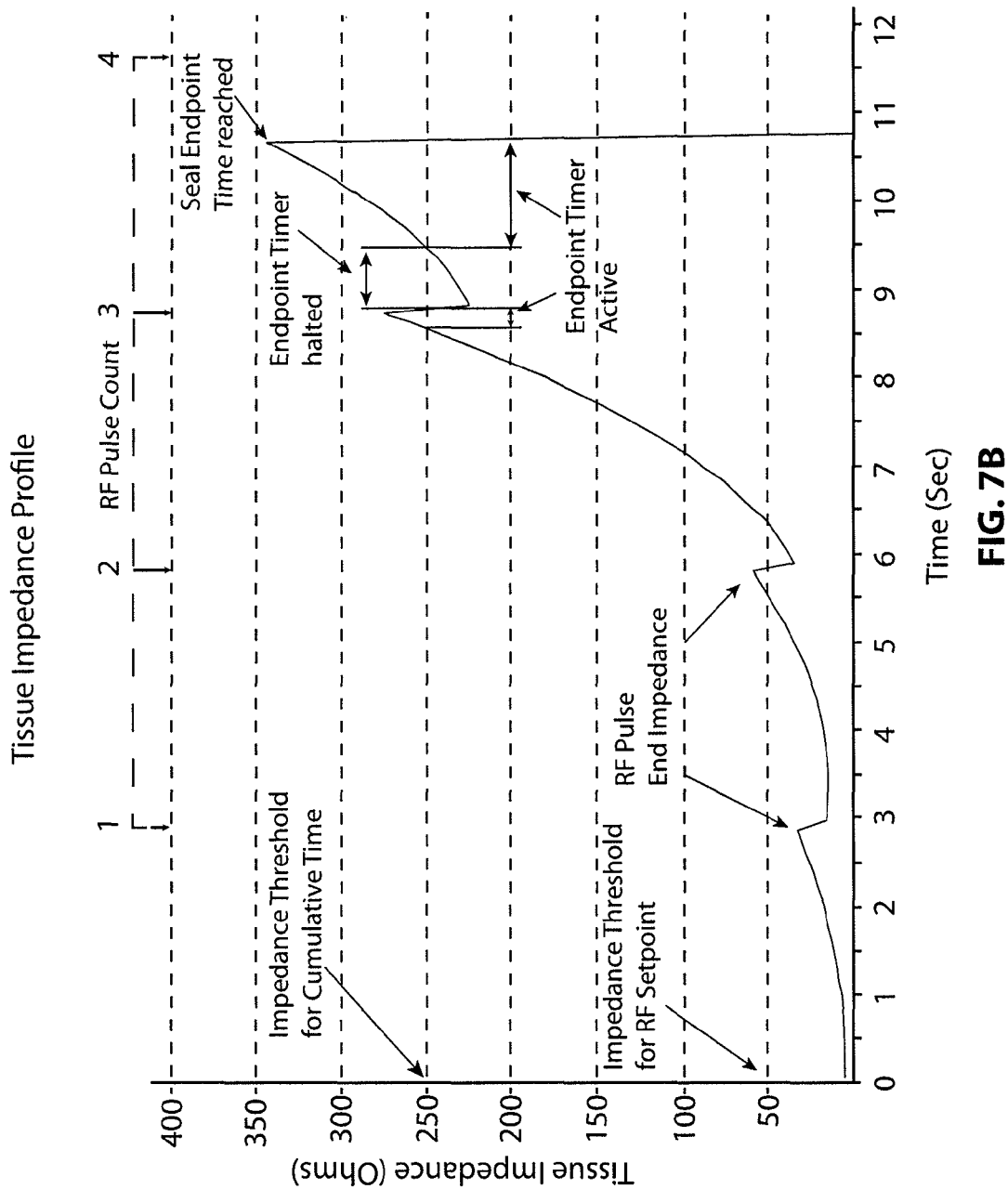
FIG. 7B is a timing diagram showing a tissue impedance profile during energy delivery according to an embodiment of the method.

FIGS. 7A and 7B are companion figures that show aspects of events underlying an electrosurgical sealing procedure that occurs in a series of four 3-second pulses, as provided by an aspect of the method. FIG. 7A shows the profile of RF energy pulses delivered during the procedure, while FIG. 7B focuses on the coincident tissue impedance profile. The length of each pulse is labeled as the RF Pulse Duration and the maximum number of pulses allowed for each seal is labeled as the Max RF Pulse Count. The following events occur during this electrosurgical tissue sealing procedure example:

1. The first RF pulse for a tissue sealing procedure starts at a power level labeled as the RF Setpoint Start Value (FIG. 7A).
2. The RF power level is increased from the RF Setpoint Start Value at a preset RF Ramping Rate until the power level reaches the upper level labeled as the RF Setpoint End Value. The RF power level remains at this value until the end of the 3-second pulse time is reached (FIG. 7A).
3. At the end of each pulse, the sensed tissue impedance value is determined and recorded as the RF Pulse End Impedance (FIG. 7B), and the power level is then set to zero (FIG. 7A).

4. For all pulses subsequent to the first, the following evaluations are made (FIGS. 7A and 7B):
   a. If the RF Pulse End Impedance is less than the Threshold for RF Setpoint, the RF power delivered is ramped at a rate identical to that of the first pulse.
   b. If the RF Pulse End Impedance is greater than the Threshold for RF Setpoint, the RF power delivered is stepped directly to the RF Setpoint End Value.

FIG. 7B shows the course of tissue impedance events that relate to controlling energy delivery and terminating the electrosurgical procedure. The sealing cycle is terminated when the tissue impedance reaches a predetermined Impedance Threshold for Cumulative Time. (A detected fault or error condition can also terminate a sealing cycle.) Stopping the sealing procedure in accordance with the cumulative sealing endpoint duration value occurs as follows:

1. Tissue impedance is determined using the signals from the RF monitoring hardware circuits.
2. When the calculated tissue impedance exceeds the Impedance Threshold for Cumulative Time (in this example, 250 Ohms), a cumulating endpoint timer is started. When the calculated tissue impedance falls below the Impedance Threshold for Cumulative Time (e.g., when a pulse completes), the endpoint timer is halted. Thus, the timer records only the total time that tissue impedance is greater than the Impedance Threshold for Cumulative Time.
3. When the timer accumulates a preset amount of time, labeled as the Seal Endpoint Time, the RF delivery is halted, the system user is notified of the completed seal and the system is placed in the ready state.

Figure 8:
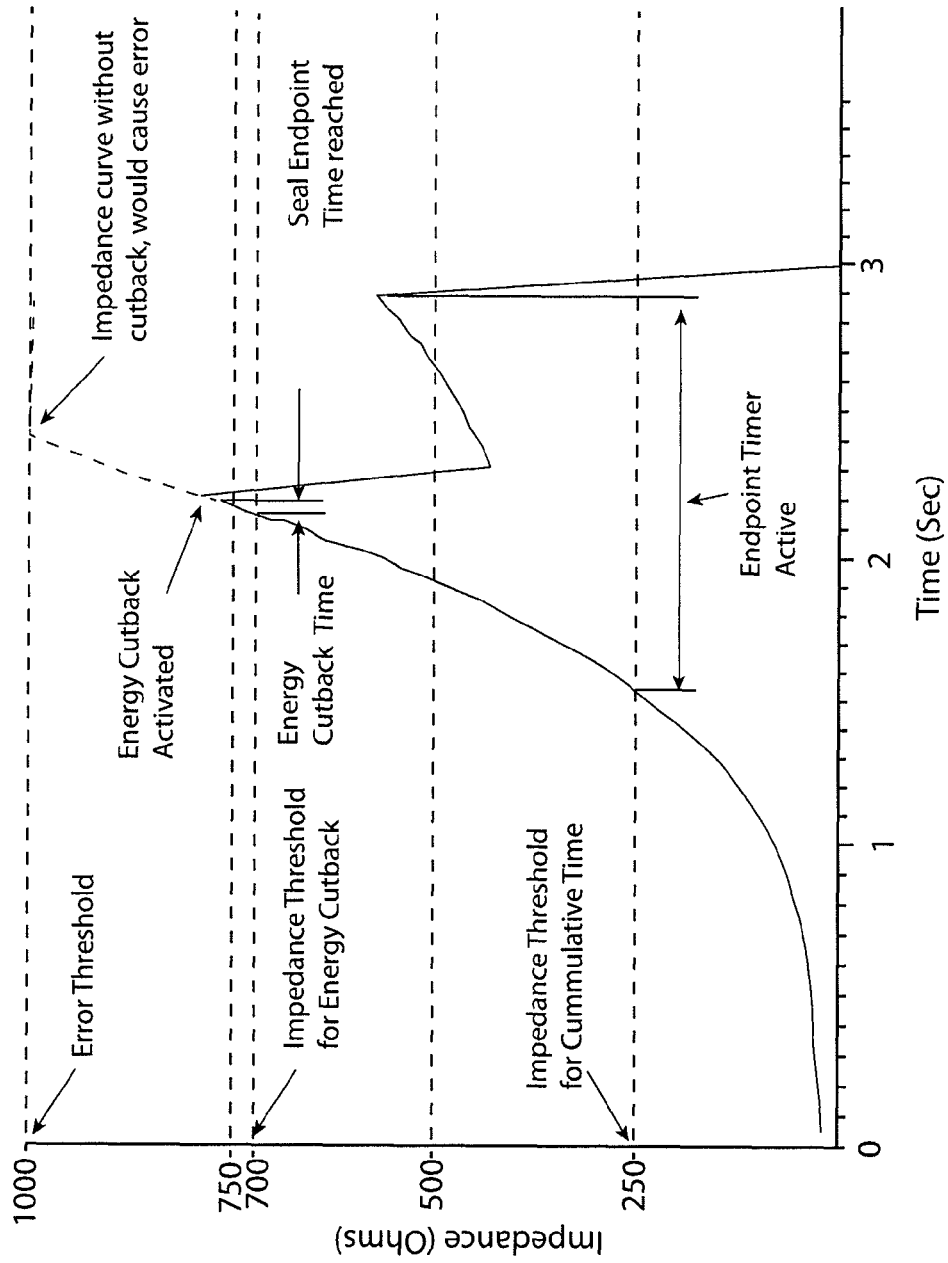
FIG. 8 is a timing diagram showing a tissue impedance profile during energy delivery as modified by the occurrence of a rapid rise in impedance that is indicative of low tissue presence in the RF circuit path.

FIG. 8 provides an example of an electrosurgical tissue sealing procedure that is modified in order to accommodate a low amount of tissue within the target locale, between the jaws of electrosurgical forceps. A relatively low amount of tissue may occur when the tissue is particularly thin (for example, 0.5 mm thickness or less) or when portions of the electrode are not in contact with any tissue. As described above, a low tissue circumstance typically creates a high impedance level. The events shown in FIG. 8 occur during a single 3-second pulse. The following steps illustrate how aspects of the method intervene to correct for low tissue presence.

1. Tissue impedance is calculated using the signals from the RF monitoring hardware circuits.
2. When the sensed tissue impedance exceeds the Impedance Threshold for Energy Cutback, for a time duration labeled as the Impedance Cutback Time (in this example, 0.1 sec), the RF delivery is reduced by decreasing the RF Voltage being delivered (see Table 1). The cutback in energy delivery is reflected in the immediate drop in sensed tissue impedance. If the tissue impedance were to exceed the Impedance Threshold for Energy Cutback a second time, the RF Voltage would be reduced again.
3. When sensed tissue impedance exceeds an Impedance Threshold for Cumulative Time (in this example, 250 ohms), an Endpoint Timer is activated. On completion of a predetermined amount of time, the Seal Endpoint Time (in this example, 1.5 seconds), as recorded by the Endpoint Timer, the electrosurgical procedure or sealing cycle is terminated.

Unless defined otherwise, all technical terms used herein have the same meanings as commonly understood by one of ordinary skill in the art of electrosurgery. Specific methods, devices, and materials are described in this application, but any methods and materials similar or equivalent to those described herein can be used in the practice of the present invention. While embodiments of the invention have been described in some detail and by way of illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices or equipment, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of the dynamics of tissue response to absorbing radiofrequency energy, consequences regarding tissue impedance, and exploiting these dynamics toward optimizing control of an electrosurgical system and method, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims appended to the patent application, including the full range of equivalency to which each element thereof is entitled.

The invention claimed is:

1. An electrosurgical system comprising:
   an RF generator configured to deliver energy through an electrosurgical device to a target tissue in a sealing cycle comprising a series of pulses, the series beginning with an initial pulse having a profile comprising a preset RF level start value that increases at a preset ramping rate to a preset RF end value; and
   a comparator configured to compare sensed impedance values of the target tissue to each of three preset impedance threshold values, these threshold values comprising a first impedance threshold value for RF setpoint, a second impedance threshold value for cumulative time, and a third impedance threshold value for energy cutback, wherein the second impedance threshold value is higher than the first impedance threshold value, and the third impedance threshold value is higher than the second impedance threshold value;
   wherein the RF generator is further configured to control the delivery of energy during the sealing cycle by responding to the comparison of the sensed impedance values to the first, second and third impedance threshold values,
   wherein when the sensed impedance is greater than the second impedance threshold value, a cumulative timing function is initiated, which accumulates time toward a preset sealing cycle duration, and when such time reaches the preset sealing cycle duration, energy delivery ceases immediately.

2. The electrosurgical system of claim 1 wherein the system is configured to cease the sealing cycle when a cumulative time of tissue showing an impedance value over the second impedance threshold value reaches a preset sealing cycle duration limit.

3. The electrosurgical system of claim 1, wherein when the sensed impedance value at the end of a preceding pulse is less than the first impedance threshold value for RF setpoint, the system is configured to control the delivery of energy to the subsequent pulse such that it has the same pulse profile as that of the initial pulse.

4. The electrosurgical system of claim 1, wherein when the sensed impedance value at the end of a preceding pulse exceeds the first impedance threshold value for RF setpoint, the system is further configured to control the delivery of energy to the subsequent pulse such that it has an elevated profile.

5. The electrosurgical system of claim 1, wherein when the sensed impedance at any time during a pulse exceeds the third impedance threshold value for energy cutback, the system is configured to cut back energy delivery.

6. An electrosurgical method comprising:
   delivering energy from an electrosurgical device to a target tissue in a sealing cycle comprising a series of pulses, the series beginning with an initial pulse having a profile comprising a preset RF level start value that increases at a preset ramping rate to a preset RF end value;
   comparing sensed impedance values of the target tissue to each of three preset impedance threshold values, these threshold values comprising a first impedance threshold value for RF setpoint, a second impedance threshold value for cumulative time, and a third impedance threshold value for energy cutback, wherein the second impedance threshold value is higher than the first impedance threshold value, and the third impedance threshold value is higher than the second impedance threshold value;
   controlling the delivery of energy during the sealing cycle by responding to the comparison of the sensed impedance values to the first, second and third impedance threshold values, wherein when the sensed impedance is greater than the second impedance threshold value, a cumulative timing function is initiated, which accumulates time toward a preset sealing cycle duration, and when such time reaches the preset sealing cycle duration, energy delivery ceases immediately.

7. The electrosurgical method of claim 6 wherein controlling the delivery of energy during the sealing cycle by responding to the comparison of the sensed impedance values to the first, second and third impedance threshold values comprises ceasing the sealing cycle when a cumulative time of tissue showing an impedance value over the second impedance threshold value reaches a preset sealing cycle duration limit.

8. The electrosurgical method of claim 6, further comprising recording a cumulative time within an ongoing sealing cycle during which the sensed tissue impedance value exceeds the second impedance threshold value for cumulative time.

9. The electrosurgical method of claim 6, further comprising sending sensed tissue impedance values to a processor throughout each pulse, each pulse being either a preceding pulse to a subsequent pulse or being a final pulse.

10. The electrosurgical method of claim 6, wherein when the sensed impedance value at the end of a preceding pulse is less than the first impedance threshold value for RF setpoint, the method further comprises controlling the delivery of energy to the subsequent pulse such that it has the same pulse profile as that of the initial pulse.

11. The electrosurgical method of claim 6, wherein when the sensed impedance value at the end of a preceding pulse exceeds the first impedance threshold for RF setpoint, the method further comprises controlling the delivery of energy to the subsequent pulse such that it has an elevated profile.

12. The electrosurgical method of claim 6, wherein when the sensed impedance at any time during a pulse exceeds the third impedance threshold for energy cutback, the method further comprises cutting back energy delivery.

13. The electrosurgical method of claim 12, wherein cutting back energy delivery comprises cutting back energy delivery immediately.

14. An electrosurgical method comprising:
   delivering energy from an electrosurgical device to a target tissue site in a sealing cycle comprising a series of pulses, each pulse of a preset pulse duration, the series of pulses beginning with an initial pulse having an initial pulse profile comprising a preset RF level start value that increases to a preset RF end value during the pulse;
   sensing tissue impedance values during each pulse, each pulse being either a preceding pulse to a subsequent pulse or being a final pulse;
   controlling the delivery of energy during a sealing cycle such that;
   a. a profile of a successor pulse relative to the profile of its preceding pulse has any of an identical profile or a higher energy profile, depending on a comparison of the impedance value shown by tissue during the first pulse against to a first preset impedance threshold value for RF setpoint,
   b. energy is cutback during a pulse when the sensed impedance value exceeds a third preset threshold value for energy cutback; and
   c. energy delivery ceases when a cumulative amount of time that sensed impedance has exceeded a second preset impedance threshold value for cumulative time has accumulated a preset sealing cycle duration limit,
   wherein the second preset impedance threshold value is higher than the first preset impedance threshold value, and the third preset impedance threshold value is higher than the second preset impedance threshold value, and
   wherein when the sensed impedance is greater than the second preset impedance threshold value, a cumulative timing function is initiated, which accumulates time toward a preset sealing cycle duration, and when such time reaches the preset sealing cycle duration, energy delivery ceases immediately.

15. The electrosurgical method of claim 14, wherein:
   when the sensed impedance exceeds the first preset impedance threshold value for RF set point, the energy profile of the succeeding pulse exceeds the energy profile of the preceding pulse, and
   when the sensed impedance is less than the first preset impedance threshold value for RF set point, the energy profile of the succeeding pulse is identical to the energy profile of the preceding pulse.

16. The electrosurgical method of claim 14, wherein the energy profile of a pulse comprises an RF start value, an RF end value, and a transition phase between the RF start value and the RF end value.

17. The electrosurgical method of claim 14, wherein a lowered pulse energy profile of a successor pulse, with respect to the preceding pulse, comprises any of a lowered RF start value, a lowered RF end value, or a lower rate of transition from the RF start value to the RF end value.

18. The electrosurgical method of claim 14, wherein a heightened energy pulse profile of a successor pulse, with respect to the preceding pulse, comprises any of a higher RF start value, a higher RF end value, or a higher rate of transition from the RF start value to the RF end value.

19. The electrosurgical method of claim 14, wherein the transition from the RF start value to the RF end value comprises any of a sloped transition or a stepped transition.

20. An electrosurgical method comprising:
delivering energy from an electrosurgical device to a target tissue in a sealing cycle comprising a series of pulses, each pulse of a preset duration, the series of pulses beginning with an initial pulse having a profile comprising a preset RF level start value that increases at a preset ramping rate to a preset RF end value;
sensing tissue impedance values throughout each pulse, each pulse being either a preceding pulse to a subsequent pulse or being a final pulse;
comparing the sensed impedance values to each of three preset impedance threshold values, these threshold values comprising a first impedance threshold value for RF setpoint, a second impedance threshold value for cumulative time, and a third impedance threshold value for energy cutback;
controlling the delivery of energy during the sealing cycle by responding to the comparison of the sensed impedance values to the first, second and third impedance threshold values, such that the sealing cycle ceases when the cumulative time of tissue showing an impedance value over the second impedance threshold value reaches a preset sealing cycle duration limit,
wherein the second impedance threshold value is higher than the first impedance threshold value, and the third impedance threshold value is higher than the second impedance threshold value, and
wherein when the sensed impedance is greater than the second impedance threshold value, a cumulative timing function is initiated, which accumulates time toward a preset sealing cycle duration, and when such time reaches the preset sealing cycle duration, energy delivery ceases immediately.

\* \* \* \* \*